(12) United States Patent
Schimke et al.

(10) Patent No.: US 10,266,830 B2
(45) Date of Patent: *Apr. 23, 2019

(54) USE OF APTAMERS IN THERAPY AND/OR DIAGNOSIS OF AUTOIMMUNE DISEASES

(71) Applicants: Charité—Universitaetsmedizin Berlin, Berlin (DE); Max-Delbrueck-Centrum fuer molekulare Medizin, Berlin (DE)

(72) Inventors: Ingolf Schimke, Berlin (DE); Annekathrin Haberland, Berlin (DE); Gerd Wallukat, Berlin (DE)

(73) Assignees: Max-Delbrueck-Centrum fuer Molekulare Medizin, Berlin (DE); Charite-Universitaetsmedizin Berlin, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/841,755

(22) Filed: Dec. 14, 2017

(65) Prior Publication Data

US 2018/0127757 A1    May 10, 2018

Related U.S. Application Data

(63) Continuation of application No. 14/977,780, filed on Dec. 22, 2015, now Pat. No. 9,862,953, which is a
(Continued)

(30) Foreign Application Priority Data

Mar. 7, 2011    (EP) ..................................... 11157229

(51) Int. Cl.
    *C12N 15/11*    (2006.01)
    *A61K 48/00*    (2006.01)
(Continued)

(52) U.S. Cl.
    CPC ......... *C12N 15/115* (2013.01); *A61M 1/3679* (2013.01); *G01N 33/564* (2013.01);
(Continued)

(58) Field of Classification Search
    CPC .............. C12N 15/115; C12N 2310/16; C12N 2320/30
See application file for complete search history.

(56) References Cited

U.S. PATENT DOCUMENTS 9,234,201 B2 *  1/2016  Schimke ............. A61M 1/3679
2007/0026029 A1 *  2/2007  Mattner ............... A61M 1/3472
                                                                                                                                                    424/423

FOREIGN PATENT DOCUMENTS

EP              1486787 A1    12/2004
WO     WO-2005037323 A2 *  4/2005  ........... C12N 15/115

OTHER PUBLICATIONS

Agonistic autoantibodies against the α1-adrenoceptor in patients with Morbus Alzheimer and vascular dementia Kunze, Rudolf Alzheimer's & Dementia: The Journal of the Alzheimer's Association, vol. 6, Issue 4, S413. Abstract p. 2-339.*
(Continued)

*Primary Examiner* — Terra C Gibbs
(74) *Attorney, Agent, or Firm* — Fox Rothschild, LLP

(57) ABSTRACT

The present invention is directed to an aptamer comprising or consisting of the nucleic acid sequence of SEQ ID No. 1, SEQ ID No. 2, SEQ ID No. 3 and/or a nucleic acid sequence being at least 80% identical to one of SEQ ID No. 1, 2 and 3 for use in therapy and/or diagnosis of autoimmune diseases, wherein the autoimmune disease is cardiomyopathy, dilated cardiomyopathy (DCM), peripartum cardiomyopathy (PPCM), idiopathic cardiomyopathy, Chagas' cardiomyopathy, Chagas' megacolon, Chagas' megaesophagus, Chagas' neuropathy, benign prostatic hyperplasia, scleroderma, psoriasis, Raynaud syndrome, pre-eclampsia, kidney
(Continued)

allograft rejection, myocarditis, glaucoma, hypertension, pulmonary hypertension, malignant hypertension, and/or Alzheimer's disease.

10 Claims, 17 Drawing Sheets

Specification includes a Sequence Listing.

Related U.S. Application Data continuation of application No. 14/003,675, filed as application No. PCT/EP2012/053616 on Mar. 2, 2012, now Pat. No. 9,234,201.

(60) Provisional application No. 61/449,772, filed on Mar. 7, 2011.

(51) Int. Cl.
*C07H 21/02* (2006.01)
*C07H 21/04* (2006.01)
*C12N 15/115* (2010.01)
*A61M 1/36* (2006.01)
*G01N 33/564* (2006.01)
*G01N 33/68* (2006.01)

(52) U.S. Cl.
CPC ..... *G01N 33/6854* (2013.01); *C12N 2310/16* (2013.01); *C12N 2310/317* (2013.01); *C12N 2310/3517* (2013.01); *C12N 2320/10* (2013.01); *C12N 2320/30* (2013.01)

(56) References Cited

OTHER PUBLICATIONS

Thathiah and Strooper (Nature Reviews, Neuroscience, Feb. 2011. vol. 12:73-87).*
Haberland et al. (Circ Res. 2011, vol. 109:986-992).*
Connor A C et al: "Aptamer stationary phase for protein capture in affinity capillary chromatography", Journal of Chromatography A, vol. 1111, No. 2, Apr. 14, 2006, pp. 115-119.

* cited by examiner

SEQUENCE LISTING

<160> NUMBER OF SEQ ID NOS: 3

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: Synthetic
      aptamer sequence 1 oligonucleotide

<400> SEQUENCE: 1
ggttggtgtg gttgg                                                      15

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: Synthetic
      aptamer sequence 2 oligonucleotide

<400> SEQUENCE: 2
cgcctaggtt gggtagggtg gtggcg                                          26

<210> SEQ ID NO 3
<211> LENGTH: 12
<212> TYPE: DNA

```
<213> ORGANISM: Artificial Sequence
<220> FEATURE:
<223> OTHER INFORMATION: Description of Artificial Sequence: Synthetic
      truncated 12mer oligonucleotide of SEQ ID No. 1

<400> SEQUENCE: 3
ggttggtgtg gt                                                             12
```

USE OF APTAMERS IN THERAPY AND/OR DIAGNOSIS OF AUTOIMMUNE DISEASES

CROSS-REFERENCE TO RELATED APPLICATIONS

This application is a continuation of U.S. application Ser. No. 14/977,780 filed on Dec. 22, 2015, now U.S. Pat. No. 9,862,953, which is a continuation of U.S. application Ser. No. 14/003,675 filed on Oct. 24, 2013, now U.S. Pat. No. 9,234,201, which is a § 371 national stage entry of International Application No. PCT/EP2012/053616 filed on Mar. 2, 2012, which claims priority to European Patent Application No. 11157229.3, filed Mar. 7, 2011, and U.S. Provisional Patent Application No. 61/449,772, filed Mar. 7, 2011, which are hereby incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Sep. 6, 2013, is named 3975-85_SL.txt and is 1253 bytes in size.

The immune system forms an essential part of every animal. Mammals make use of its immune system in the defence against microorganisms, in detection and removal of aberrant cells like e.g. tumor cells, and in regeneration of tissue. Thereby the organism relies on two interconnected defence mechanisms, humoral and cellular immunity.

Antibodies, when bound to its antigen are triggers of the humoral immune response. Antibodies can act in multiple ways. Apart from neutralisation of the antigen, antibodies also activate the complement system. There are also antibodies which are directed to antigens of the own body. As reason for the generation of such so called autoantibodies, molecular mimicry and/or bystander activation are seen. Specific binding of the autoantibodies to own antigens can activate natural killer cells (NK cells) which are able to facilitate degradation of these antigens.

Autoimmune diseases are based on such specific recognition and binding of antibodies directed to own constituent parts of the body which triggers an immune response against own cells or tissues. Apart from this immunostimmulatory effect, autoantibodies can contribute to the development of pathogenic phenotypes also by other mechanisms. It is well known that there are also autoantibodies which can be specific for the extracellular part of G-protein coupled receptors such as: adrenergic alpha-1 receptor, adrenergic beta-1 receptor, adrenergic beta-2 receptor, endothelin1 ETA receptor, muscarinic $M_2$ receptor, angiotensin II AT1 receptor and/or proteinase activated receptors (PAR) receptors and, upon specific binding, can activate or block these receptors. The presence of such autoantibodies in an organism can lead to agonistic or antagonistic effects in the sense of a permanent activation or blockade of the respective receptors which could play a role in the development of the disease.

Dilated cardiomyopathy (DCM) is one of the diseases in that a high percentage of the patients present with such activating autoantibodies binding to extracellular parts of the adrenergic beta-1 receptor, in particular to the 1st or 2nd loop of adrenergic beta-1 receptor. Consequently, an autoimmune pathogenesis of DCM in these patients was suggested. Upon binding of these autoantibodies the receptors are continuously activated (Jahns et al. (2004) Direct evidence for a beta-1-adrenergic receptor-directed autoimmune attack as a cause of idiopathic cardiomyopathy. J. Clin. Invest. 113, 1419 to 1429).

In recent studies, it could be shown that removal of these autoantibodies from the blood via immunoglobulin adsorption contributes to regeneration of the heart muscle (Wallukat G, Reinke P, Dörffel W V, Luther H P, Bestvater K, Felix S B, Baumann G. (1996) Removal of autoantibodies in dilated cardiomyopathy by immunoadsorption. Int J Cardiol. 54:191-195; Müller J, Wallukat G, Dandel M, Bieda H, Brandes K, Spiegelsberger S, Nissen E, Kunze R, Hetzer R (2000) Immunoglobulin adsorption in patients with idiopathic dilated cardiomyopathy. Circulation. 101:385-391. W. V. Dörffel, S. B. Felix, G. Wallukat, S. Brehme, K. Bestvater, T. Hofmann, F K Kleber, G. Baumann, P. Reinke (1997) Short-term hemodynamic effects of immunoadsorption in dilated cardiomyopathy. Circulation 95, 1994-1997 and W. V. Dörffel, G. Wallukat, Y. Dörffel, S. B. Felix, G. Baumann (2004) Immunoadsorption in idiopathic dilated cardiomyopathy, a 3-year follow-up. Int J. Cardiol. 97, 529-534).

There are other diseases of the cardiovascular system which were suggested to be in relation to the presence of autoantibodies against G-protein coupled receptors such as, Chagas cardiomyopathy, peripartum cardiomyopathy, myocarditis, pulmonary hypertension and malignant hypertension. Autoantibodies against G-protein coupled receptors were also found in patients e.g. with glaucoma, Diabetes mellitus, Alzheimer disease, benign prostatic hyperplasia, scleroderma, Raynaud syndrome, psoriasis, and pre-eclampsia and in chronic Chagas disease as well as those with kidney allograft rejection.

It is an object of the present invention to provide novel modalities for use in therapy and/or diagnosis of autoimmune diseases that are associated with the presence of autoantibodies in the patient.

The present invention provides an aptamer comprising or consisting of the nucleic acid sequence of SEQ ID No. 1, SEQ ID No. 2, SEQ ID No. 3 and/or a nucleic acid sequence being at least 80% identical to one of SEQ ID No. 1, 2 and 3 for use in therapy and/or diagnosis of autoimmune diseases.

The aptamers of the invention are characterized in that they comprise or consist of a nucleic acid sequence of 15 nucleotides with SEQ ID No. 1, SEQ ID No. 2, SEQ ID No. 3 and/or a nucleic acid sequence being at least 80% identical to one of SEQ ID No. 1, 2 and 3. The 15-mer: GGT TGG TGT GGT TGG (SEQ ID No. 1), the 26-mer: CGC CTA GGT TGG GTA GGG TGG TGG CG (SEQ ID No. 2) and the 12-mer: GGT TGG TGT GGT (SEQ ID No. 3) are all independently from each other capable of and responsible for the target specificity of the aptamer of the invention. Further nucleic acid molecules or sequences can be added to the 5'- and/or to the 3'-end of the nucleic acid sequence with SEQ ID No. 1, 2 and/or 3. Said 15-mer (SEQ ID No. 1) has first been isolated for its binding to thrombin, see U.S. Pat. No. 5,543,293, which holds also true for the 26-mer (SEQ ID No. 2) which was first described in WO/2010/033167. The first mentioned has already been used under the name ARC183 in clinical phase I trials for inhibition of thrombin, i.e. as an anticoagulant for potential use in acute cardiovascular settings. The 26-mer has been used under the name NU172 (ARC 2172) in a clinical phase II trial (clinical trial gov. identifier: NCT 00808964). However, it turned out for the 15-mer (SEQ. ID No. 1) that the amount of aptamer needed to achieve the desired anticoagulation resulted in a sub-optimal dosing profile.

It has surprisingly been found that the aptamers of the invention can be used to interfere with the interaction of antibodies, in particular of autoantibodies, specific for G-protein coupled receptors associated with autoimmune diseases. In particular it could be shown that aptamers of the invention are capable of binding to autoantibodies specific for adrenergic alpha-1 receptor, adrenergic beta-1 receptor, adrenergic beta-2 receptor, endothelin 1 ETA receptor, muscarinic $M_2$ receptor, angiotensin II AT1 receptor, and/or PAR receptors and of inhibiting the specific interaction of these autoantibodies with its target proteins. By inhibiting these interactions, the aptamers of the invention diminish or even abolish the permanent activation of the respective G-protein coupled receptors without the need for removal of these antibodies. Thus, the present invention provides compounds that are described the first time for their suitability for use in treatment and/or diagnosis of autoimmune diseases, in particular of autoimmune diseases associated with the presence of autoantibodies which recognize G-protein coupled receptors, namely autoimmune diseases associated with the presence of autoantibodies specific for adrenergic alpha-1 receptor, adrenergic beta-1 receptor, adrenergic beta-2 receptor, endothelin 1 ETA receptor, muscarinic $M_2$ receptor, angiotensin II AT1 receptor, and/or PAR receptors. Furthermore after immobilization, the aptamers of the invention are capable of catching the autoantibiodies indicated above. This way, a platform is provided $1^{st}$ to establish an apheresis technology for clearing patient's serum from the autoantibodies and $2^{nd}$ to develop an analytical tool for the measurement of the autoantibodies. The last can be used in particular for diagnosis of autoimmune diseases.

For the purpose of this invention, the term "aptamer" refers to an oligonucleotide that comprises or consists of the nucleic acid sequence SEQ ID No. 1, SEQ ID No. 2, SEQ ID No. 3 and/or a nucleic acid sequence being at least 80% identical to one of SEQ ID No. 1, 2 and 3 and is capable of binding specifically and with high affinity to a particular target molecule, e.g. to an autoantibody directed against a G-protein coupled receptor like e.g. adrenergic alpha-1 receptor, adrenergic beta-1 receptor, adrenergic beta-2 receptor, endothelin 1 ETA receptor, muscarinic $M_2$ receptor, angiotensin II AT1 receptor, and/or PAR receptors.

The aptamer of the invention comprises or consists of a sequence of nucleic acid molecules, the nucleotides. The aptamer of the invention preferably comprises unmodified and/or modified D- and/or L-nucleotides. According to the common one letter code of nucleic acid bases "C" stands for cytosine, "A" stands for adenine, "G" stands for guanine, and "T" stands for thymine, whereas "U" stands for uracil. If not indicated below to the contrary, the term "nucleotide" shall refer to ribonucleotides and desoxyribonucleotides. Respectively the terms "2'-fluoro-modified nucleotide", "2'-methoxy-modified nucleotide", and/or "2-amino-modified nucleotide" refers to modified ribonucleotides and modified desoxyribonucleotides.

An aptamer is considered to consist or comprise a nucleic acid sequence being at least 80% identical to one of SEQ ID No. 1, 2 and 3, if said aptamer comprises a contiguous sequence of nucleotides that shows at least 80% sequence identity over the whole length of SEQ ID No. 1, 2 or 3 to the nucleotide sequence of SEQ ID No. 1, 2 or 3, respectively. Means to determine sequence identity are well known in the art and may comprise e.g. the use of the algorithm blastn.

The aptamer of the invention can comprise a nucleic acid sequence of ≥15 nucleotides to ≤160 nucleotides, preferably of ≥15 nucleotides to ≤120 nucleotides.

The aptamer of the invention can comprise or consist of a DNA- or an RNA-nucleotide sequence and, thus, can be referred to as DNA-aptamer or RNA-aptamer respectively. It is understood that, if the aptamer of the invention comprises an RNA-nucleotide sequence, within the sequence motifs specified throughout the present invention thymin is replaced by uracil. The RNA-nucleotide sequences of the present invention are identical with the DNA-nucleotide sequences of the invention with the proviso that T is replaced by U. For the sake of conciseness throughout the present invention reference is made solely to explicit DNA-nucleotide sequences. However, it is understood that the respective RNA-nucleotide sequences are also comprised by the present invention.

The use of DNA-aptamers is particularly preferred. DNA-aptamers are usually more stable in plasma than RNA-aptamers.

The aptamers of the invention may comprise a nucleotide sequence containing 2'-modified nucleotides, e.g. 2'-fluoro-, 2'-methoxy- and/or 2'-amino-modified nucleotides. The aptamer of the invention may also comprise a mixture of desoxyribonucleotides, modified desoxyribonucleotides, ribonucleotides and/or modified ribonucleotides.

The aptamer of the invention may comprise modifications. Such modifications encompass e.g. alkylation, i.e. methylation, arylation or acetylation of at least one nucleotide, the inclusion of enantiomers and/or the fusion of aptamers with one or more other nucleotides or nucleic acid sequences. Such modifications may comprise e.g. 5'- and/or 3'-CAP-modifications or 5'- and/or 3_PEG structures. Alternatively or in addition the aptamer of the invention may comprise modified nucleotides, preferably selected from locked-nucleic acids, 2'-fluoro-, 2'-methoxy- and/or 2'-amino-modified nucleotides.

Locked nucleic acids (LNA) represent analogons of the respective RNA nucleotides wherein the conformation has been fixed. Oligonucleotides of locked nucleic acids comprise one or more bicyclic ribonucleosides, wherein the 2'-OH group is connected with the C4-carbon atom via a methylen group. Locked nucleic acids exhibit an improved stability versus nucleases compared to the respective unmodified RNA-aptamer counterparts. Also the hybridisation properties are improved which allows for an enhancement of affinity and specificity of the aptamer.

Another preferred modification is the addition of a so called 3'-CAP-, a 5'-CAP-structure and/or of a modified guanosin-nucleotide (e.g. 7-methyl-guanosin) to the 3'- and/or 5'-end of the aptamer. Such a modification of the 3'- and/or 5'-end has the effect that the aptamer is protected from a fast degradation by nucleases.

Alternatively or in addition, the aptamer of the invention can exhibit a pegylated 5'-end and/or 3'-end. A 5'-PEG and/or 3'-PEG modification comprises the addition of at least one polyethylene glycol (PEG) unit, preferably the PEG group comprises 1 to 900 ethylene groups, more preferably from 1 to 450 ethylene groups. In a preferred embodiment, the aptamer comprises linear PEG units with HO—$(CH_2CH_2O)_n$—H, wherein n is an integer of 1 to 900, preferably n is an integer of 1 to 450.

The aptamer of the invention can comprise or consist of a nucleic acid sequence with a phospho-thioate backbone or can be wholly or in part configured as a peptide nucleic acid (PNA).

One advantage of modifying the aptamer of the invention by one or more of the ways mentioned above is that the aptamer can be stabilized against detrimental influences like e.g. nucleases present in the environment wherein the aptamer is used. Said modifications are also suitable to adapt the pharmacological properties of the aptamer. The modifications preferably do not alter the affinity or specificity of the aptamer.

The aptamer of the invention may also be conjugated to a carrier molecule and/or to a reporter molecule. Carrier molecules comprise such molecules that, when conjugated to the aptamer, prolong the plasma half life of the conjugated aptamer in human plasma, e.g. by enhancing the stability and/or by affecting the excretion rate. One example of a suitable carrier molecule is PEG. Reporter molecules comprise molecules that allow for the detection of the conjugated aptamer. Examples of such reporter molecules are GFP, biotin, cholesterol, dyes like e.g. fluorescence dyes, electrochemically active reporter molecules and/or compounds comprising radioactive residues, in particular radionuclides suitable for PET (positron emission tomography) detection like e.g. $^{18}F$, $^{11}C$, $^{13}N$, $^{15}O$, $^{82}Rb$ or $^{68}Ga$. The skilled person is well aware of suitable carrier and reporter molecules and of ways of how to conjugate them to the aptamer of the invention.

The aptamer of the invention inhibits the agonistic or blocking effect of an antibody. For the purpose of the present invention, the term "antibody" refers to naturally occurring antibodies, including e.g. autoantibodies in particular autoantibodies of a patient suffering from an autoimmune disease related to the presence of autoantibodies specific for a G-protein coupled receptor like e.g. adrenergic alpha-1 receptor, adrenergic beta-1 receptor, adrenergic beta-2 receptor, endothelin 1 ETA receptor, muscarinic $M_2$ receptor, angiotensin II AT1 receptor, and/or PAR receptors, and modified or genetically engineered antibodies. An autoantibody is an antibody manufactured by the immune system of an individual that is directed against one or more of the individual's own proteins. However, the term antibody is not limited to an antibody with the classical heavy and light chain architecture. The terms "antibody" or "antibodies" as used herein are art-recognized terms and are understood to refer to molecules or active fragments of molecules that bind to given antigens, particularly the terms refer to immunoglobulin molecules and to immunologically active portions of immunoglobulin molecules, i.e. molecules that contain a binding site that specifically binds an antigen. An immunoglobulin is a protein comprising one or more polypeptides substantially encoded by the immunoglobulin kappa and lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Also subclasses of the heavy chain are known. For example, IgG heavy chains in humans can be any of IgG1, IgG2, IgG3 and IgG4 subclass. The antibody can preferably be of IgM and/or IgG class or any subclass thereof (IgG1, IgG2, IgG3, IgG4).

"Antibodies" are intended within the scope of the present invention to include autoantibodies, monoclonal antibodies, polyclonal antibodies, chimeric, single chain, bispecific, simianized, human and humanized antibodies as well as active fragments thereof. Examples of active fragments of molecules that bind to known antigens include separated light and heavy chains, Fab, Fab/c, Fv, Fab', and F(ab')2 fragments, including the products of an Fab immunoglobulin expression library and epitope-binding fragments of any of the antibodies and fragments mentioned above.

The aptamers of the invention are used in treatment and/or diagnosis of autoimmune diseases. As used for the purpose of the present invention, the term "autoimmune disease" or "autoimmune diseases" refers to autoimmune diseases, in particular to autoimmune diseases in a human, wherein the autoimmune diseases are associated with the presence of autoantibodies specific for a G-protein coupled receptor. Said autoantibodies may preferably be involved in the pathogenesis of the autoimmune disease and, as such, may be present in the serum of a patient suffering from said autoimmune disease. More preferably the autoimmune diseases are autoimmune diseases associated with the presence in the serum of the patient of autoantibodies specific for adrenergic alpha-1 receptor, adrenergic beta-1 receptor, adrenergic beta-2 receptor, endothelin 1 ETA receptor, muscarinic $M_2$ receptor, angiotensin II AT1 receptor, and/or PAR receptors. Even more preferred, the autoimmune disease is cardiomyopathy, dilated cardiomyopathy (DCM), peripartum cardiomyopathy (PPCM), idiopathic cardiomyopathy, Chagas' cardiomyopathy, Chagas' megacolon, Chagas' megaesophagus, Chagas' neuropathy, benign prostatic hyperplasia, scleroderma, psoriasis, Raynaud syndrome, pre-eclampsia, kidney allograft rejection, myocarditis, glaucoma, hypertension, pulmonary hypertension, malignant hypertension, and/or Alzheimer's disease. Most preferably the term "autoimmune disease" or "autoimmune diseases" refers to the autoimmune diseases dilated cardiomyopathy (DCM), peripartum cardiomyopathy (PPCM), Chagas' cardiomyopathy, Chagas' megacolon, glaucoma, hypertension, pulmonary hypertension, malignant hypertension, kidney allograft rejection, Raynaud syndrome and/or Alzheimer's disease.

The manufacturing or mass production of aptamers of the invention is well known in the art and represents a mere routine activity.

The present invention is also directed to a pharmaceutical composition comprising at least one aptamer of the invention and, optionally, at least one pharmaceutically acceptable excipient. The invention is also directed to a pharmaceutical composition comprising an aptamer of the invention or a mixture of different aptamers of the invention and a pharmaceutically acceptable excipient like e.g. a suitable carrier or diluent.

Preferably the aptamer of the invention constitutes an active ingredient of the pharmaceutical composition and/or is present in an effective amount.

The term "effective amount" denotes an amount of the aptamer of the invention having a prophylactically, diagnostically or therapeutically relevant effect on a disease or pathological conditions. A prophylactic effect prevents the outbreak of a disease. A therapeutically relevant effect relieves to some extent one or more symptoms of a disease or returns to normal either partially or completely one or more physiological or biochemical parameters associated with or causative of the disease or pathological conditions. The respective amount for administering the aptamer of the invention is sufficiently high in order to achieve the desired prophylactic, diagnostic or therapeutic effect. It will be understood by the skilled person that the specific dose level, frequency and period of administration to any particular mammal will depend upon a variety of factors including the activity of the specific components employed, the age, body weight, general health, sex, diet, time of administration, route of administration, drug combination, and the severity of the specific therapy. Using well-known means and methods, the exact amount can be determined by one of skill in the art as a matter of routine experimentation.

In the pharmaceutical composition of the invention at least 20% of the total aptamer content is made of an aptamer of the invention, preferably at least 50%, more preferably at least 75%, most preferable at least 95%.

When used for therapy, the pharmaceutical composition will generally be administered as a formulation in association with one or more pharmaceutically acceptable excipients. The term "excipient" is used herein to describe any ingredient other than the aptamer of the invention. The choice of excipient will to a large extent depend on the particular mode of administration. Excipients can be suitable carriers and/or diluents.

The pharmaceutical composition of the invention may be administered orally. Oral administration may involve swallowing, so that the composition enters the gastrointestinal tract, or buccal or sublingual administration may be employed by which the composition enters the blood stream directly from the mouth.

Formulations suitable for oral administration include: solid formulations such as tablets; coated tablets, capsules containing particulates, liquids, or powders; lozenges (including liquid-filled); and chews; multi- and nano-particulates; gels; solid solutions; liposomes; films, ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

For tablet dosage forms, depending on dose, the aptamer of the invention may make up from 0.1 weight % to 80 weight % of the dosage form, more typically from 5 weight % to 60 weight % of the dosage form. In addition to the aptamer of the invention, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Tablets may comprise additional excipients like e.g. binders, surface active agents, lubricants and/or other possible ingredients like e.g. anti-oxidants, colorants, flavouring agents, preservatives and/or taste-masking agents.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

Solid formulations for oral administration may be formulated to be immediate and/or modified release. Modified release formulations include delayed-, sustained-, pulsed-, controlled-, targeted and programmed release.

The pharmaceutical composition of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of pharmaceutical composition of the invention used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLApoly(dl-lactic-coglycolic)acid (PGLA) micro spheres.

The pharmaceutical composition of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated. Other means of topical administration include delivery by electroporation, iontophoresis, phonophoresis, sonophoresis and microneedle or needle-free (e.g. Powderject™, Bioject™, etc.) injection. Formulations for topical administration may be formulated to be immediate and/or modified release. Modified release formulations include delayed-, sustained-, pulsed-, controlled-, targeted and programmed release.

For administration to human patients, the total daily dose of the aptamer of the invention and/or the pharmaceutical composition of the invention is typically in the range 0.001 mg to 5000 mg depending, of course, on the mode of administration. For example, an intravenous daily dose may only require from 0.001 mg to 40 mg. The total daily dose may be administered in single or divided doses and may, at the physician's discretion, fall outside of the typical range given herein.

These dosages are based on an average human subject having a weight of about 65 kg to 70 kg. The physician will readily be able to determine doses for subjects whose weight falls outside this range, such as infants and the elderly.

The present invention also encompasses a kit comprising an aptamer of the invention, a pharmaceutical composition, a container and optionally written instructions for use and/or with means for administration.

The aptamer, the pharmaceutical composition and/or the kit of the invention are used in therapy and/or diagnosis of autoimmune diseases, in particular of autoimmune diseases in a human. Preferably, the autoimmune diseases are autoimmune diseases associated with the presence of autoantibodies specific for a G-protein coupled receptor, wherein the autoantibodies are present in the serum of a patient suffering from said autoimmune disease. More preferably the autoimmune diseases are autoimmune diseases associated with the presence in the serum of the patient of autoantibodies specific for adrenergic alpha-1 receptor, adrenergic beta-1 receptor, adrenergic beta-2 receptor, endothelin 1 ETA receptor, muscarinic $M_2$ receptor, angiotensin II AT1 receptor, and/or PAR receptors. Even more preferred, the autoimmune disease is cardiomyopathy, dilated cardiomyopathy (DCM), peripartum cardiomyopathy (PPCM), idiopathic cardiomyopathy, Chagas' cardiomyopathy, Chagas' megacolon, Chagas' megaesophagus, Chagas' neuropathy, benign prostatic hyperplasia, scleroderma, psoriasis, Raynaud syndrome, pre-eclampsia, kidney allograft rejection, myocarditis, glaucoma, hypertension, pulmonary hypertension, malignant hypertension, and/or Alzheimer's disease. Most preferably the term "autoimmune disease" or "autoimmune diseases" refers to the autoimmune diseases dilated cardiomyopathy (DCM), peripartum cardiomyopathy (PPCM), Chagas' cardiomyopathy, Chagas' megacolon, glaucoma, hypertension, pulmonary hypertension, malignant hypertension, kidney allograft rejection, Raynaud syndrome and/or Alzheimer's disease.

The terms "therapy", "treatment" and "therapeutically," as used herein, refer to the act of treating, as "treating" is defined below. As used herein, the term "treating" refers to reversing, alleviating or inhibiting the progress of a disease, disorder or condition, or one or more symptoms of such disease, disorder or condition, to which such term applies. As used herein, "treating" may also refer to decreasing the probability or incidence of the occurrence of a disease, disorder or condition in a mammal as compared to an untreated control population, or as compared to the same mammal prior to treatment. For example, as used herein, "treating" may refer to preventing a disease, disorder or condition, and may include delaying or preventing the onset of a disease, disorder or condition, or delaying or preventing the symptoms associated with a disease, disorder or condition. As used herein, "treating" may also refer to reducing the severity of a disease, disorder or condition or symptoms associated with such disease, disorder or condition prior to a mammal's affliction with the disease, disorder or condition. Such prevention or reduction of the severity of a disease, disorder or condition prior to affliction relates to the administration of the composition of the present invention, as described herein, to a subject that is not at the time of administration afflicted with the disease, disorder or condition. As used herein "treating" may also refer to preventing the recurrence of a disease, disorder or condition or of one or more symptoms associated with such disease, disorder or condition.

For treatment and/or diagnosis of a disease, irrespective of the route of administration, the aptamer of the invention is administered at a daily dose per treatment cycle of not more than 20 mg/kg body weight, preferably of not more than 10 mg/kg body weight, more preferably selected from the range of 1 µg/kg to 20 mg/kg body weight, most preferably selected from a range of 0.01 to 10 mg/kg body weight.

The present invention is also directed to the use of an aptamer of the invention or pharmaceutical composition of the invention in the manufacture of a medicament for treatment and/or diagnosis of an autoimmune disease. Preferably the autoimmune disease is cardiomyopathy, dilated cardiomyopathy (DCM), peripartum cardiomyopathy (PPCM), idiopathic cardiomyopathy, Chagas' cardiomyopathy, Chagas' megacolon, Chagas' megaesophagus, Chagas' neuropathy, benign prostatic hyperplasia, scleroderma, psoriasis, Raynaud syndrome, pre-eclampsia, kidney allograft rejection, myocarditis, glaucoma, hypertension, pulmonary hypertension, malignant hypertension, and/or Alzheimer's disease. Even more preferably the term "autoimmune disease" or "autoimmune diseases" refers to the autoimmune diseases dilated cardiomyopathy (DCM), peripartum cardiomyopathy (PPCM), Chagas' cardiomyopathy, Chagas' megacolon, glaucoma, hypertension, pulmonary hypertension, malignant hypertension, kidney allograft rejection, Raynaud syndrome and/or Alzheimer's disease.

In another aspect, the present invention is directed to a method of treatment or diagnosis of an autoimmune disease, wherein an individual in need of such treatment is administered an effective amount of an aptamer of the invention or a pharmaceutical composition of the invention. Preferably the autoimmune disease is cardiomyopathy, dilated cardiomyopathy (DCM), peripartum cardiomyopathy (PPCM), idiopathic cardiomyopathy, Chagas' cardiomyopathy, Chagas' megacolon, Chagas' megaesophagus, Chagas' neuropathy, benign prostatic hyperplasia, scleroderma, psoriasis, Raynaud syndrome, pre-eclampsia, kidney allograft rejection, myocarditis, glaucoma, hypertension, pulmonary hypertension, malignant hypertension, and/or Alzheimer's disease. Even more preferably the term "autoimmune disease" or "autoimmune diseases" refers to the autoimmune diseases dilated cardiomyopathy (DCM), peripartum cardiomyopathy (PPCM), Chagas' cardiomyopathy, Chagas' megacolon, glaucoma, hypertension, pulmonary hypertension, malignant hypertension, kidney allograft rejection, Raynaud syndrome and/or Alzheimer's disease.

The aptamer of the invention, when used for treatment or diagnosis of an autoimmune disease does not necessarily need to be administered to an individual or patient. The therapeutic or diagnostic effect may also be achieved by use of the aptamer of the invention for elimination of antibodies, like e.g. autoantibodies from the body or from body fluids. Such an elimination may comprise the application of the aptamer of the invention in a setting where the aptamer of the invention is contacted with a body fluid solely ex vivo, e.g. during immune adsorption and/or apheresis, so that the aptamer of the invention does not enter the body of the individual or patient to be treated. Thus, the present invention is also directed to an apheresis column comprising an aptamer of the invention.

Apheresis is a medical technology in which the blood of a donor or patient is passed through an apparatus that separates out one particular constituent and returns the remainder back to the circulation of the donor or patient. The aptamer of the invention can be used as selective ingredient during apheresis. The selective ingredient is responsible for specifically separating out the desired particular constituents, namely the antibodies or autoantibodies present in the sample or blood which are specifically targeted by the aptamer of the invention. Preferably the aptamer of the invention is used as selective ingredient in therapeutic apheresis of blood or parts thereof derived from a patient suffering from an autoimmune disease. More preferably the autoimmune disease is cardiomyopathy, dilated cardiomyopathy (DCM), peripartum cardiomyopathy (PPCM), idiopathic cardiomyopathy, Chagas' cardiomyopathy, Chagas' megacolon, Chagas' megaesophagus, Chagas' neuropathy, benign prostatic hyperplasia, scleroderma, psoriasis, Raynaud syndrome, pre-eclampsia, kidney allograft rejection, myocarditis, glaucoma, hypertension, pulmonary hypertension, malignant hypertension, and/or Alzheimer's disease. Even more preferably the term "autoimmune disease" or "autoimmune diseases" refers to the autoimmune diseases dilated cardiomyopathy (DCM), peripartum cardiomyopathy (PPCM), Chagas' cardiomyopathy, Chagas' megacolon, glaucoma, hypertension, pulmonary hypertension, malignant hypertension, kidney allograft rejection, Raynaud syndrome and/or Alzheimer's disease.

The present invention also relates to an aptamer of the invention coupled to a solid support. The skilled person is well aware of techniques and materials which may be used to produce such aptamers coupled to a solid support. In a preferred embodiment, the solid support comprises a solid material that is applicable in medical, biochemical or biological assays, like e.g. materials used in apheresis or ELISA assays. Said solid material comprises polymers that are usually used as support in medical, biochemical or biological assays. In particular the aptamer of the invention may be coupled to a solid support that allows for the use of the resulting product in the manufacturing of a column suitable for apheresis, preferably a column that is suitable for use in an apheresis to remove antibodies that can be specifically bound by the aptamer of the invention from a liquid sample, preferably from a body fluid.

In a further aspect, the present invention is directed to the use of an aptamer of the invention for the in vitro detection and/or characterization of antibodies, like e.g. autoantibodies, being specific for a G-protein coupled receptor, preferably the G-protein coupled receptors adrenergic alpha-1 receptor, adrenergic beta-1 receptor, adrenergic beta-2 receptor, endothelin 1 ETA receptor, muscarinic $M_2$ receptor, angiotensin II AT1 receptor, and/or PAR receptors.

Such a use may comprise the testing of a sample in a rat cardiomyocyte beating frequency assay in the presence and absence of an effective amount of an aptamer of the invention. Depending on the effect of the sample and the aptamer of the invention on the beating frequency, the skilled person can conclude on the presence of respective antibodies. Data on total or relative quantity of such antibodies in the sample may also be gained as well as on other properties of such antibodies.

The so called rat cardiomyocyte beating frequency assay is a well established assay for detection and characterization of antibodies, e.g. autoantibodies derived from patients, specific for a number of human G-protein coupled receptors like e.g. human adrenergic alpha-1 receptor, adrenergic beta-1 receptor, adrenergic beta-2 receptor, endothelin 1 ETA receptor, muscarinic $M_2$ receptor, angiotensin II AT1 receptor, and/or PAR receptors. The assay is described in detail in Wallukat et al. (1987) Effects of the serum gamma globulin fraction of patients with allergic asthma and dilated cardiomyopathy on chromotropic beta adrenoceptor function in cultured neonatal rat heart myocytes, *Biomed. Biochim. Acta* 46, 634-639; Wallukat et al. (1988) Cultivated cardiac muscle cells—a functional test system for the detection of autoantibodies against the beta adrenergic receptor, *Acta Histochem.* Suppl. 35, 145-149; and Wallukat et al. (2010) Distinct patterns of autoantibodies against G-protein coupled receptors in Chagas' cardiomyopathy and megacolon. Their potential impact for early risk assessment in asymptomatic Chagas' patients, *J. Am. Coll. Cardiol.* 55, 463-468. Thus, the skilled person is well aware of the nature of this assay and knows how to apply it.

The aptamer of the invention can particularly be used in detection and/or characterization of respective antibodies, wherein the antibodies are presented in or derived from a body fluid, preferably a fluid of the human body, more preferably of human blood, plasma, serum, urine, feces, synovial fluid, interstitial fluid, lymph, saliva, sudor, spinal fluid and/or lacrimal fluid. In a preferred embodiment, the body fluid is taken from an individual suffering from or suspected to suffer from an autoimmune disease. Preferably the autoimmune disease is cardiomyopathy, dilated cardiomyopathy (DCM), peripartum cardiomyopathy (PPCM), idiopathic cardiomyopathy, Chagas' cardiomyopathy, Chagas' megacolon, Chagas' megaesophagus, Chagas' neuropathy, benign prostatic hyperplasia, scleroderma, psoriasis, Raynaud syndrome, pre-eclampsia, kidney allograft rejection, myocarditis, glaucoma, hypertension, pulmonary hypertension, malignant hypertension, and/or Alzheimer's disease. Even more preferably the term "autoimmune disease" or "autoimmune diseases" refers to the autoimmune diseases dilated cardiomyopathy (DCM), peripartum cardiomyopathy (PPCM), Chagas' cardiomyopathy, Chagas' megacolon, glaucoma, hypertension, pulmonary hypertension, malignant hypertension, kidney allograft rejection, Raynaud syndrome and/or Alzheimer's disease.

For detection and/or characterization of such antibodies, the aptamer of the invention may be used in solution or in an immobilized form.

The aptamer of the invention may be used for direct or indirect detection and/or characterization of said antibodies.

In the following the invention will be further explained and exemplified by way of examples.

FIGURES

FIGS. 4A, 4B, 4C and 4D show the binding of the thrombin-aptamer (SEQ. ID No. 1) on the immobilized ETA-AB, the immobilized rabbit IgG and the immobilized human IgG-subclasses for control. 4A and 4C: 25 nM of each protein immobilized, 4B and 4D: 250 nM of the proteins immobilized. 4A and 4B: binding of the thrombin-aptamer SEQ. ID No. 1 and 4C and 4D: binding of its scrambled control sequence. The biotinylated thrombin-aptamer was used and the biotin moiety served for detection. The amount of bound biotin was quantified via Neutravidin-POD and the $TMB/H_2O_2$-reaction.

Figure 5:
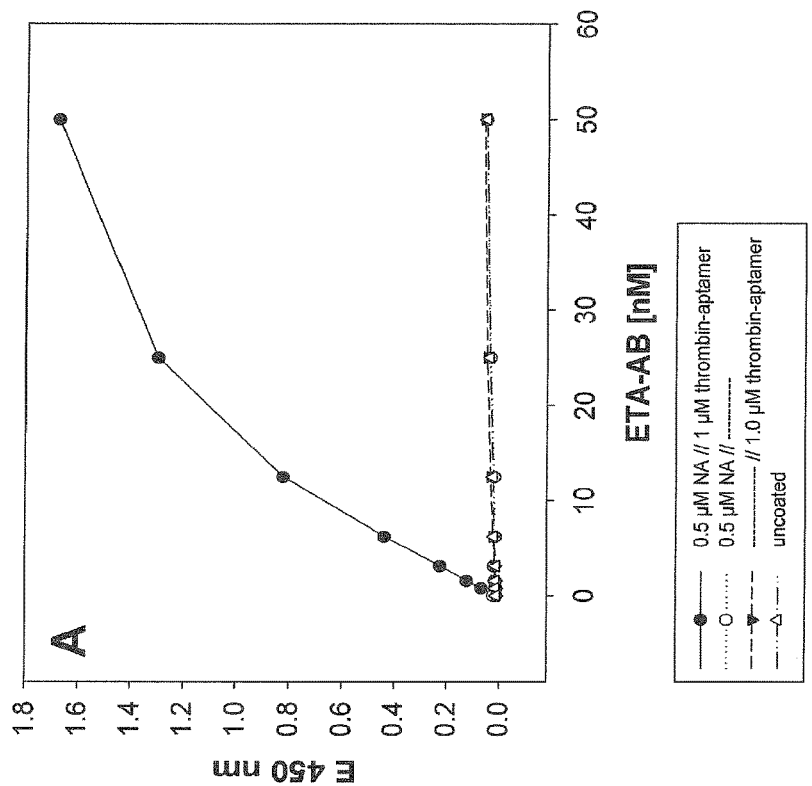
Figure 5:
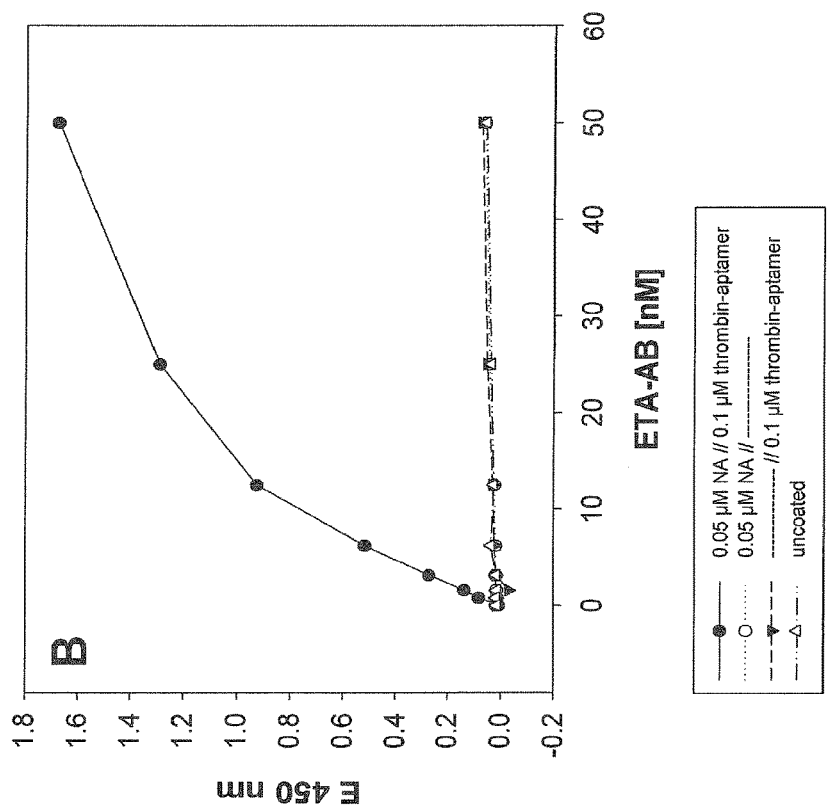

FIGS. 5A and 5B show the binding of the ETA-AB (SP 4122P) onto immobilized thrombin-aptamer (SEQ. ID No. 1) 5A: 1 µM 5B: 0.1 µM thrombin-aptamer for immobilization. For detection served the secondary anti-rabbit IgG-POD antibody (1:10.000) and the $TMB/H_2O_2$-reaction. The uncoated and the Neutravidine-coated plate served for control. (Neutravidine=NA).

Figure 6:
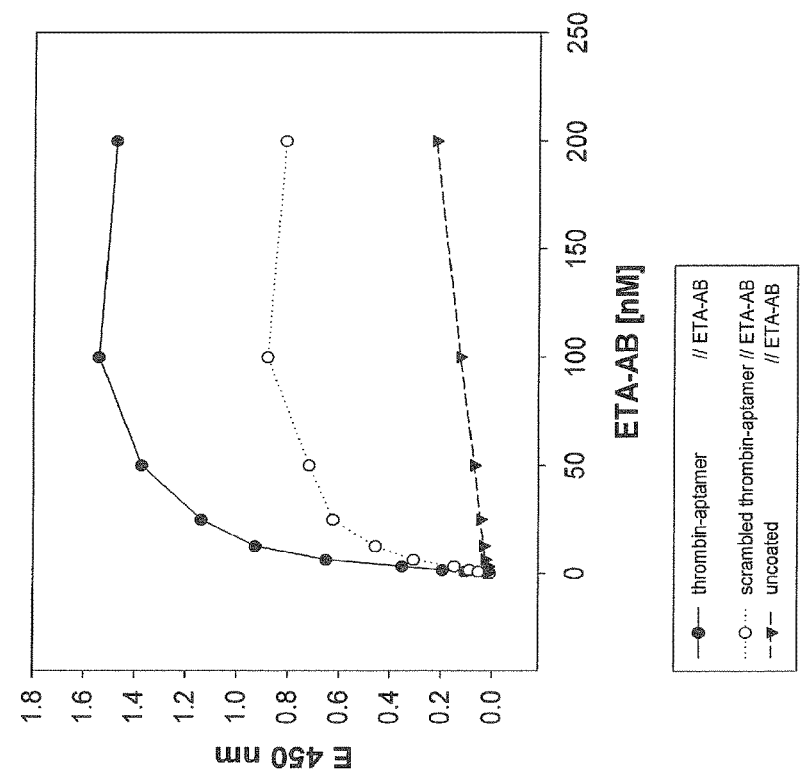

FIG. 6 shows the binding of the ETA-AB (SP 4122P) onto immobilized thrombin-aptamer (SEQ. ID No. 1) and the immobilized scrambled thrombin-aptamer for control.

Figure 7:
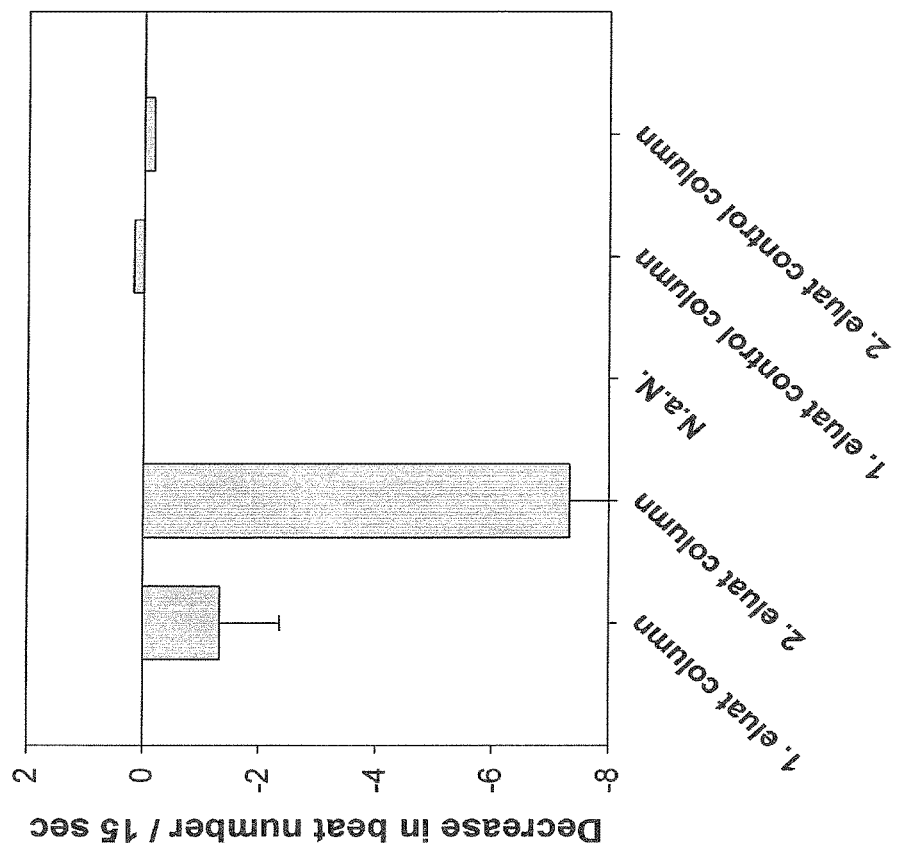

FIG. 7 shows the recovery of the bound ETA-AB after elution from the thrombin-aptamer column and the corresponding control experiment (control column). The ETA-AB activity was measured in the bioassay.

Figure 8:
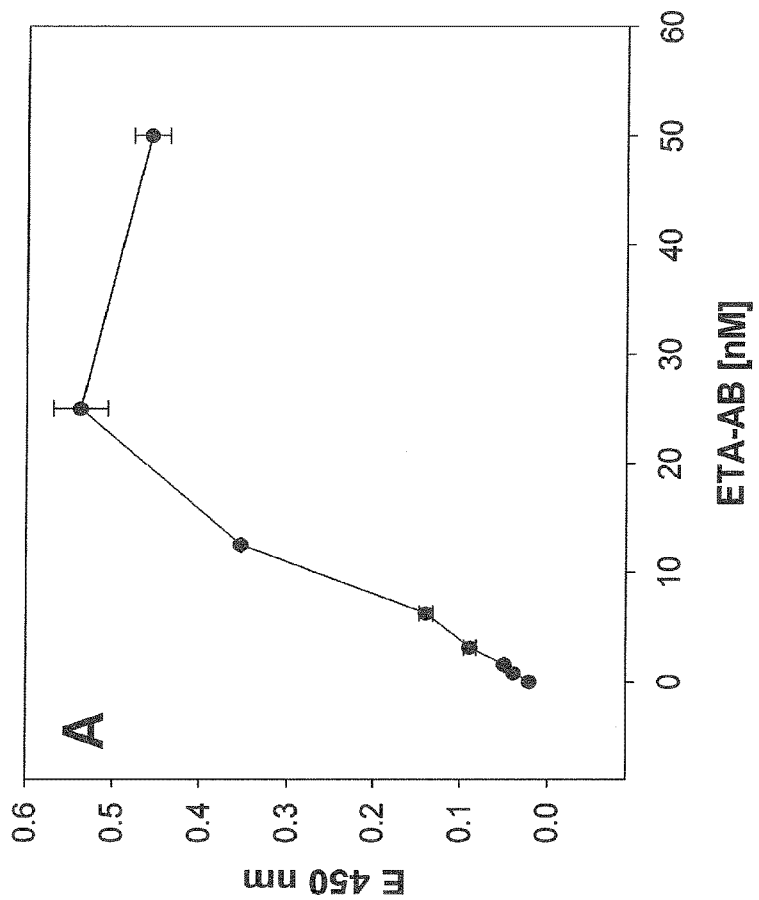
Figure 8:
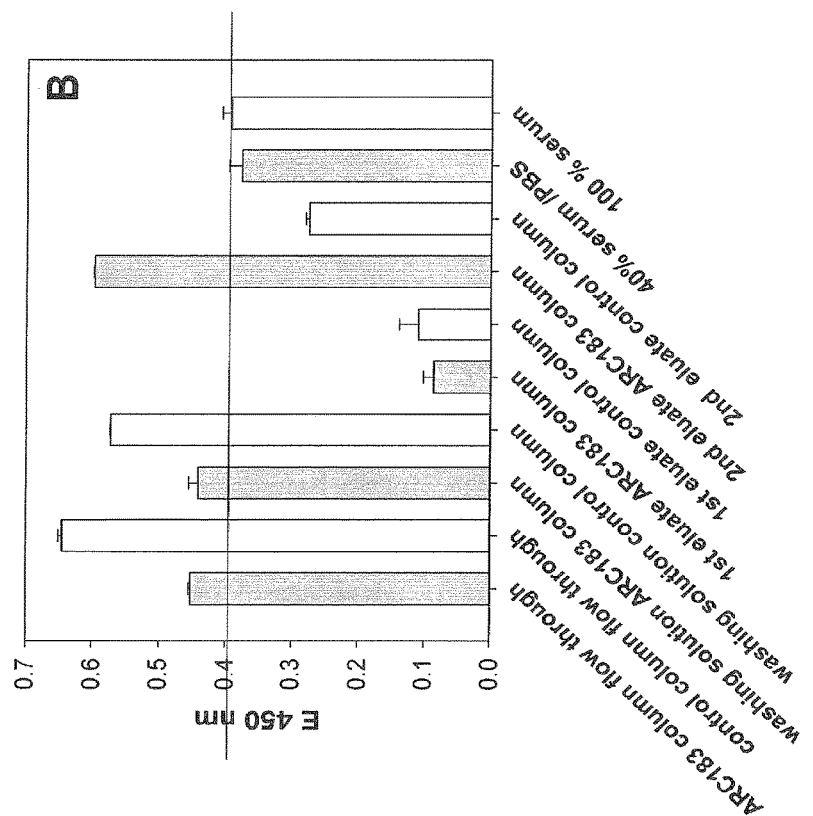

FIGS. 8A and 8B show the recovery of the ETA-AB from the spiked serum in the ELISA experiment. 8A: shows the ETA-AB standard curve which was treated comparably to the eluate samples (dialysis). 8B: shoes the amount of recovered ETA-AB in the flow-throughs, the washing solution and the eluates after elution from the thrombin-aptamer column (ARC183 column) and the corresponding control column (scrambled thrombin-aptamer). For detection served an anti-rabbit-IgG-POD antibody (1:10,000) and the TMB/$H_2O_2$ detection.

FIG. 9 shows the testing of AAB-neutralization capacity of the 5'-FITC-labelled thrombin-aptamer using the bioassay of spontaneously beating neonatale rat cardiomyocytes. The increase of beating frequency caused by beta1-receptor AABs was reduced by about 50% when 100 nM FITC-thrombin-aptamer was present. The bars are the mean of two independent experiments (n=2).

FIG. 10 shows the detection of ETA-AAB of a patient sample using an thrombin-aptamer//FITC-thrombin-aptamer sandwich assay. For control served a control IgG sample and scramble thrombin-aptamer. The data are from one experiment. (FITC-throm-a=FITC-thrombin-aptamer, throm-apta=thrombin-aptamer).

FIG. 11 shows the neutralization of AAB activity (beta1-receptor AAB, alpha1+beta2-receptor AAB, affinity purified beta2-receptor AAB, each AAB n=1) by 100 nM dT-thrombin-aptamer, measured in the bioassay of spontaneously beating neonatale cardiomyocytes.

FIG. 12 shows testing of the functionality of the truncated thrombin-aptamer sequence (12-mer sequence, SEQ ID No. 3, Throm K1) compared to the original 15-mer sequence (ARC183, SEQ ID No. 1) and the 26-mer sequence (NU172, SEQ ID No. 2) neutralizing the positive chronotropic activity of beta1-receptor AABs in the bioassay of spontaneously beating rat cardiomyocytes.

EXAMPLES

Summary

The aptamers consisting of a nucleic acid sequence with SEQ. ID No. 1 and 2, respectively, are affine and specific binders for autoantibodies which target the G-protein coupled receptors. The aptamers are able to neutralize the AAB (autoantibody)-function in the soluble state. Immobilized onto surfaces the aptamers were able to capture AABs. A following elution will remove the captured AABs.

It has therefore been shown that aptamers of the present invention are appropriate molecules for therapeutic and diagnostic purposes for the treatment of diseases which are associated to functional active AABs against G-protein coupled receptors.

Material and Methods

Cardiomyocyte Preparation and Culturing

Hearts of 1 to 3 day old rats were removed under sterile conditions and transferred to phosphate buffered saline solution (PBS) containing penicillin/streptomycin. The ventricle tissue was separated, dissected in pieces and washed twice with 10 ml PBS containing penicillin/streptomycin and at last once with PBS only. The ventricle pieces were suspended in 30 ml PBS containing 0.2% trypsin. After incubation for 20 min at 37° C., the trypsination was stopped with 10 ml ice-cold heat-inactivated calf serum. The resulting suspension was centrifuged at 130×g for 6 min and the pellet transferred to 20 ml of SM20-I medium. For cell count estimation, 100 μl of this suspension was added to 100 μl trypanblue solution. For cell culturing $2.4\times10^6$ cells were suspended in 2.5 ml of glucose containing SM 20-I medium which was equilibrated with humid air and supplemented with 10% heat-inactivated calf serum, 0.1 mU insulin, and 2 μM fluorodeoxyuridine (preventing the overgrowth of the myocytes by non-myocytes), transferred to 12.5-$cm^2$ Falcon flasks and cultured as monolayers for 4 days at 37° C. The medium was renewed after two days.

Bioassay Principle

For the identification and quantification of the AAB, a bioassay was used which was firstly established for the measurement of AAB against G-protein coupled receptors by Wallukat and Wollenberger (Wallukat G, Wollenberger A. Effects of the serum gamma globulin fraction of patients with allergic asthma and dilated cardiomyopathy on chronotropic beta adrenoceptor function in cultured neonatal rat heart myocytes. Biomed Biochim Acta 1987; 46:S634-9) and which we recently described in detail for the measurement of AAB against the adrenergic beta1 and beta2- and the muscarinergic $M_2$-receptors in chronic Chagas disease (Wallukat G, Muñoz Saravia S G, Haberland A, Bartel S, Araujo R, Valda G, Duchen D, Diaz Ramirez I, Borges A C, Schimke I. Distinct patterns of autoantibodies against G-protein-coupled receptors in Chagas' cardiomyopathy and megacolon. Their potential impact for early risk assessment in asymptomatic Chagas' patients. J Am Coll Cardiol. 2010; 55:463-8.).

In this bioassay, the chronotropic response of spontaneously beating cultured neonatal rat cardiomyocytes was recorded which is the sum of positive chronotropy caused by stimulating AAB such as the ones targeting adrenergic beta1- and beta2-receptors or the adrenergic alpha1-receptor and negative chronotropy caused by inhibiting AAB such as the ones targeting muscarinergic M2-receptors or the endothelin receptor type A (ETA-receptor) (1 unit of AAB activity=1 beat/min frequency change).

To differentiate the AAB species with respect to their contribution to the chronotropic response (positive or negative chronotropy), the analysis was conducted in the presence of specific antagonists such as ICI-118.551 for beta2-receptor AAB, atropine for M2-AAB, propranolol for beta1/beta2-receptor AAB, BQ 610 or BQ 123 for the ETA-receptor, prazosine for the alpha1-adrenoceptor and Ibesartan or Losartan for the AT1-receptor. The remaining activity change is caused by AAB except the once which were specifically blocked.

A further characterization of different receptor AABs demonstrated above was done by using the AAB-epitope-representing-peptides corresponding to the extracellular loops of the receptors.

The bioassay can detect and quantify all human serum AAB and other molecules which target receptors on the cell surface whose sequences are homologue to the human receptors (in the case of AAB targeting) and which are linked to a machinery regulating the beating frequency (contractility, chronotropy) of the cells such as the G-protein system.

Preparation of Serum Samples for AAB Identification and Differentiation and AAB Activity Measurement 1 ml of control and patient serum and 660 μl saturated ammonium sulfate solution were mixed (final concentration 40% ammonium sulphate) and incubated for 18 hours at 4° C. After centrifugation for 15 min at 6,000×g, the pellet was re-suspended in 750 μl PBS, mixed with 750 μl saturated ammonium sulfate solution (final concentration 50% ammonium sulfate) and centrifuged again. After this, the pellet was suspended in 700 μl PBS and dialyzed against the 100 fold volume of PBS. The resulting IgG fraction can be stored at −20° C. until measurement.

Results
Inhibition of AAB Functionality of Different AABs Against G-Protein Coupled Receptors by Specific-Aptamers In the following the neutralization of the activity of antibodies (autoantibodies from patient serum) by the aptamer SEQ. ID No. 1 (also known as thrombin-aptamer SEQ ID No. 1, or ARC 183, described in U.S. Pat. No. 5,543,293) and by the aptamer SEQ. ID No. 2 (also known as thrombin-aptamer SEQ ID No. 2, or ARC 2172 or NU 172, described in WO/2007/025049) was investigated (Table 1).

Doing this the following antibodies (autoantibodies=AAB) were investigated: the adrenergic alpha 1-receptor AAB, the adrenergic beta1-receptor AAB, beta2-receptor AAB, the muscarinic $M_2$-receptor-AAB, the endothelin 1 ETA receptor-AAB (ETA-AAB), the angiotensin II AT1-receptor-AAB, and the PAR-receptor AAB.

The occurrence of such AAB has been described in the following pathological situations, not excluding other pathological situations which might also be carriers of the same or similar AABs: DCM, Chagas' cardiomyopathy, chronic Chagas' disease, Chagas' megacolon, Peripartum cardiomyopathy, Glaucom, pulmonary hypertension hypertension, hypertension, maligne hypertension, diabetis mellitus, Alzheimer disease, kidney allograft rejection, Raynaud Syndrome. Table 1 shows that the functional activity of all the tested autoantibodies directed against G-protein coupled receptors was neutralized using the aptamer with SEQ. ID No. 1 or partially neutralized using the aptamer with SEQ ID No. 2.

TABLE 1

Shows the capacity of the aptamers SEQ. ID No. 1 and SEQ. ID No. 2 [100 nM] on the neutralization of the functional activity of AABs directed against G-protein coupled receptors. The functional activity of the AAB was measured via their capacity to change the pulse rate of the cells [Δ beat rate/15 sec].

| disease | AAB-Typ | Loop | Affi-purified | | Without aptamer | +Thrombin-aptamer (SEQ. ID No. 1) | +scramble aptamer | +Thrombin-aptamer (SEQ. ID No. 2) |
|---|---|---|---|---|---|---|---|---|
| DCM | Beta1-receptor-AAB | 1. Loop | | Patient 1 | 6.33 | −0.17 | | |
| | | | | Patient 2 | 5.33 | 0.5 | | |
| | Beta1-receptor-AAB | 2. Loop | | Patient 1 | 5.33 | 0.17<br>0.33 | 5.33 | |
| Glaucom | Beta2-receptor-AAB | 2. Loop | Affi | Patient 1 | 7.33 | 0.33 | | 5.33 |
| | | | | Patient 2 | 8.67 | −0.17 | | |
| | | | | Patient 3 | 6.0 | 0.67 | | |
| | | | | Patient 4 | 7.67 | −0.17 | | |
| Peripartum-cardiomyopathy | Beta1-receptor-AAB | 2. Loop | Affi | Patient 1 | 6.33 | 0.5 | | 4.0 |
| Pulmonary Hypertension | Alpha1-receptor AAB | 2. Loop | | Patient 1 | 5.5 | −0.17 | | 2.0 |
| | | | | Patient 2 | 5.17 | 0.33 | | |
| | Endothelin-receptor-AAB | 2. Loop | | Patient 1 | −4.83 | −0.17 | | 2.0 |
| | | | | Patient 2 | −4.8 | 0.33 | | |
| Hypertension | Alpha1-receptor-AAB | 2. Loop | Affi | Patient 1 | 5.5 | 1.0 | | 3.33 |
| | | | | Patient 2 | 6.33 | −0.83 | | |
| Malignant. Hypertension | AT1-receptor-AAB | 2. Loop | | Patient 1 | 7.83 | 0.67 | | |
| Chagas Megacolon | Beta2-receptor-AAB | 2. Loop | | Patient 1 | 6.17 | −0.5 | | 2.0 |
| Chagas Cardiomyopathy | Beta1-receptor-AAB | 2. Loop | | Patient 2 | 3.5 | 0.5 | | 3.0 |
| | M2-receptor-AAB | 2. Loop | | Patient 2 | −3.67 | 0.5 | | 3.0 |
| Kidney transplant. | AT1-receptor-AAB | 2. Loop | Affi | Patient 1 | 6.17 | 0.17 | | |
| Diabetes mellitus | Alpha1-receptor-AAB | | | Patient 1 | 3.97 | 0.0 | | |
| | | | | Patient 2 | 5.5 | 0.33 | | |
| Alzheimer disease | Alpha1-/beta2-receptor-AAB | 2. Loop | | Patient 1 | 8.0 | 0.0 | | |
| | Beta2-receptor-AAB | 1. Loop | Affi | Patient 2 | 4.67 | 0.67 | | |

TABLE 1-continued

Shows the capacity of the aptamers SEQ. ID No. 1 and SEQ. ID No. 2 [100 nM] on the neutralization of the functional activity of AABs directed against G-protein coupled receptors. The functional activity of the AAB was measured via their capacity to change the pulse rate of the cells [Δ beat rate/15 sec].

| disease | AAB-Typ | Loop | Affi-purified | Without aptamer | +Thrombin-aptamer (SEQ. ID No. 1) | +scramble aptamer | +Thrombin-aptamer (SEQ. ID No. 2) |
| --- | --- | --- | --- | --- | --- | --- | --- |
| Raynaud Syndrome | ETA-receptor AAB | | Patient 1 | −5.17 | 0.33, 0.0, | | |
| | PAR-receptor-AAB | | Patient 1 | 7.33 | 0.17 | | |
| | | | Patient 2 | 4.67 | −0.33, 0.0 | | |

Dose-Response Curves of the Thrombin-Aptamer Mediated AAB-Neutralization

Figure 1:
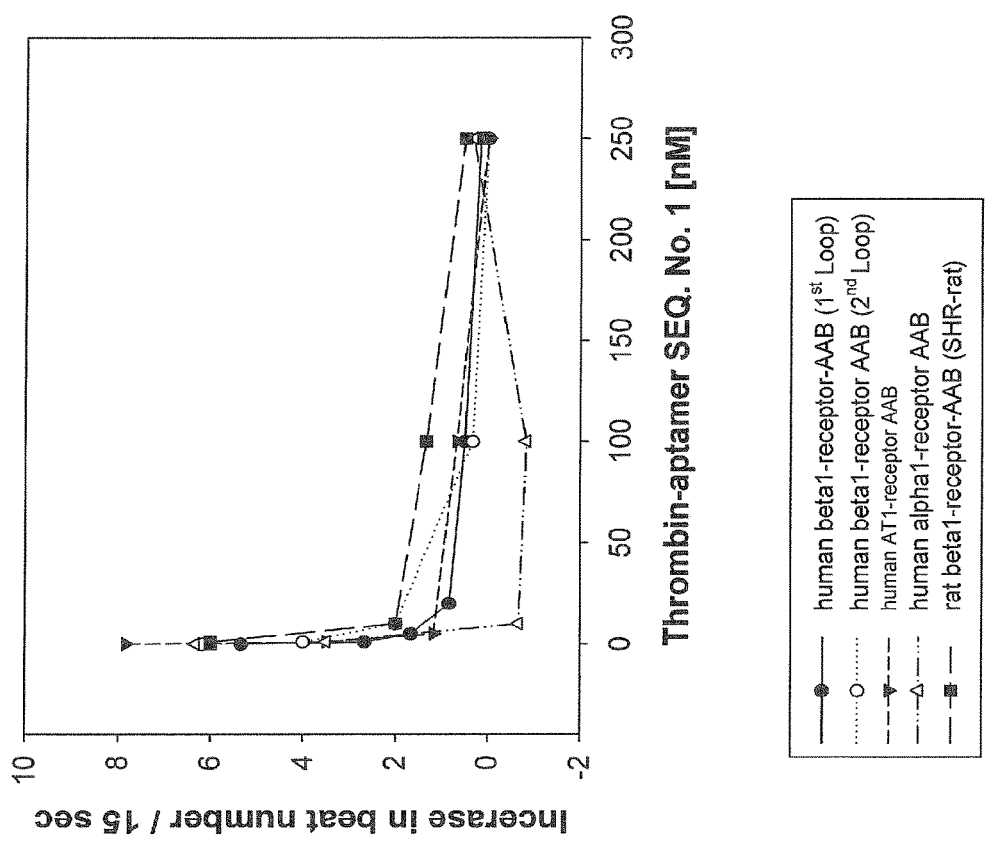
FIG. 1 shows the dose-response curves of the neutralization of the functional activity of different AABs as indicated in the figure.

In the following the dose-response curves of the single thrombin-aptamer-incubations were measured (FIG. 1). Doing this not only human AABs against G-protein coupled receptors were neutralized, but also beta1-receptor AABs from the blood of SHR-rats. In fact, human AABs against the first or second loop of the beta1-receptor, AABs against the AT1-receptor, and the adrenergic alpha1-receptor were neutralized. The beta1-receptor AAB in rats is a spontaneously formed AAB.

It became quite obvious that the different dose-response curves showed slightly differences. While the neutralization effect was most efficient for the human alpha 1-receptor AAB, it showed the smallest efficiency for the rat-beta1-receptor AAB. Taken the AAB concentration might be around 0.1% of the IgG fraction (personal information Dr. Wallukat) than the different aptamer concentrations would face a final concentration of about 1.4 nM AAB (normal IgG concentration about 10 g/l=68.5 µM, AAB dilution in the cell cultivation medium 1:50). This way it becomes very logical that the neutralization effect starts at some AAB such as the alpha 1-receptor AAB at an aptamer concentration of about 1 nM, while in general 100 nM aptamer are necessary for a complete inhibition of the AAB functionality.

Aptamer—AAB Affinity in the Presence of Competing Human IgG-3

Former experiments testing the affinity of the thrombin-aptamer SEQ ID No. 1 towards the human IgG-subtypes had shown that the thrombin-aptamer SEQ ID No. 1 had a higher affinity towards IgG-3 followed by IgG-4, IgG-2, and IgG1. While the differences between the last three subtypes were only marginal, the affinity towards the subtype IgG-3 was striking (data not shown).

Figure 2:
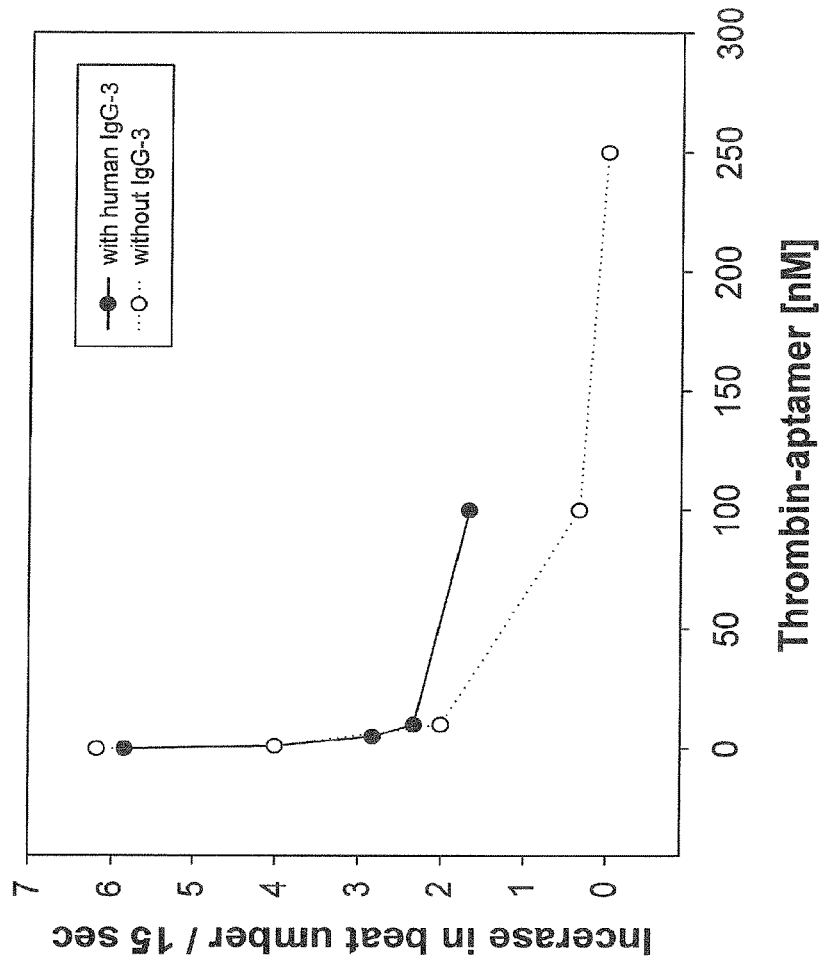
FIG. 2 shows the influence of the presence of human IgG-3 [73 nM] on the dose-response curve neutralizing the functional activity of beta1-receptor AABs by the thrombin-aptamer.

Now, in order to test, if the affinity of the thrombin-aptamer SEQ ID No. 1 towards the AAB is higher compared to its common affinity towards the IgG-3 subclass, the following competition experiment was carried out: while measuring the dose-response curve of the thrombin-aptamer SEQ ID No. 1 against a human patient serum AAB (beta1-receptor AAB, second loop, dilution 1:50), in one experimental set 73 nM human IgG-3 was added allowing to compete with the beta1-receptor AAB about the thrombin-aptamer-binding (FIG. 2). Especially at the low concentration of the thrombin-aptamer SEQ ID No. 1 (1, 5, and 10 nM thrombin-aptamer) at which the IgG-3 concentration is clearly in the molar excess to the thrombin-aptamer, no differences were observed between AAB-neutralization effects, with and without the presence of IgG-3.

Demonstration of the Binding Between the Thrombin-Aptamer and the Autoantibody Using a Model Autoantibody: Rabbit Anti-Human-Endothelinreceptor Antibody Against the Second Extracellular Loop of the Receptor (Acris Antibodies, SP 41222P)

1. ETA-AB Functionality Testing in the Bioassay and Neutralization by the Thrombin-Aptamer SEQ ID No. 1

Figure 3:
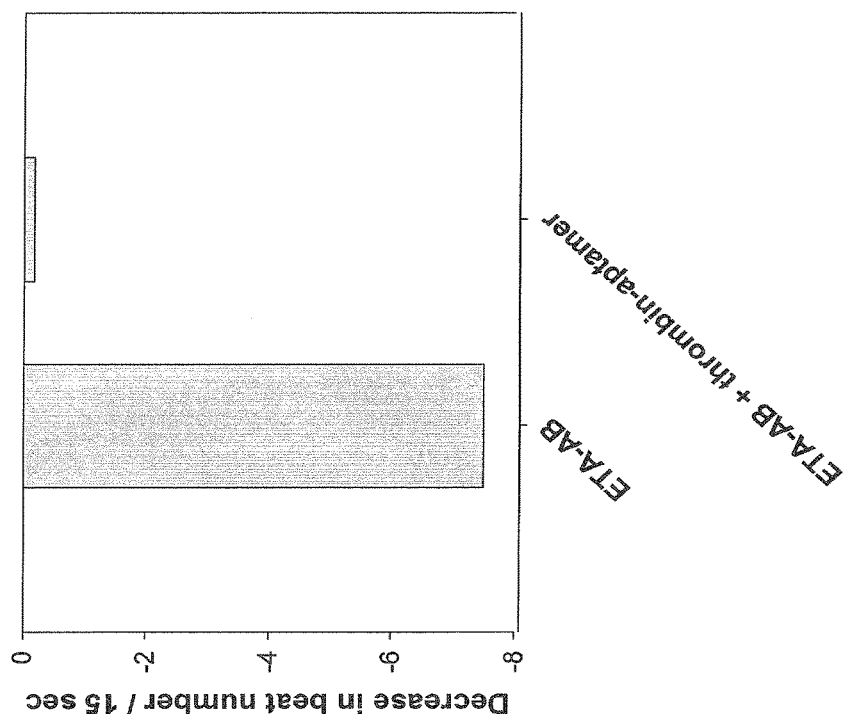
FIG. 3 shows the influence of the thrombin-aptamer on the ETA-AB mediated decrease of the beating frequency of neonatale cardiomyocytes.

The rabbit endothelinreceptor antibody (ETA-AB) was generated against the second extracellular loop of the human endothelin receptor. The antibody showed functional activity in the bioassay. The ETA-AB caused a reduction of the beating frequency of spontaneously beating neonatale rat cardiomyocytes (FIG. 3). The addition of 100 nM thrombin-aptamer caused the complete neutralization of this ETA-AB caused change in the beating frequency (FIG. 3). The addition of the thrombin-aptamer (SEQ. No. 1) alone onto the neonatale rat cardiomyocytes did nor cause any visual effect onto the cells nor did it influence on the basal beating frequency (data not shown).

2. Testing the Direct Binding Between the Thrombin-Aptamer SEQ ID No. 1 and the ETA-AB Testing the direct binding between the thrombin-aptamer and the ETA-AB in the ELISA-experiment two different experimental set-ups were tested. Firstly the ETA-AB was immobilised onto the ELISA plate and its ability to bind the thrombin-aptamer SEQ ID No. 1 was tested (FIGS. 4A-4D). In a second set of experiments the thrombin-aptamer SEQ ID No. 1 was immobilised and the ETA-AB was offered for binding (FIGS. 5A, 5B).

Figure 4:
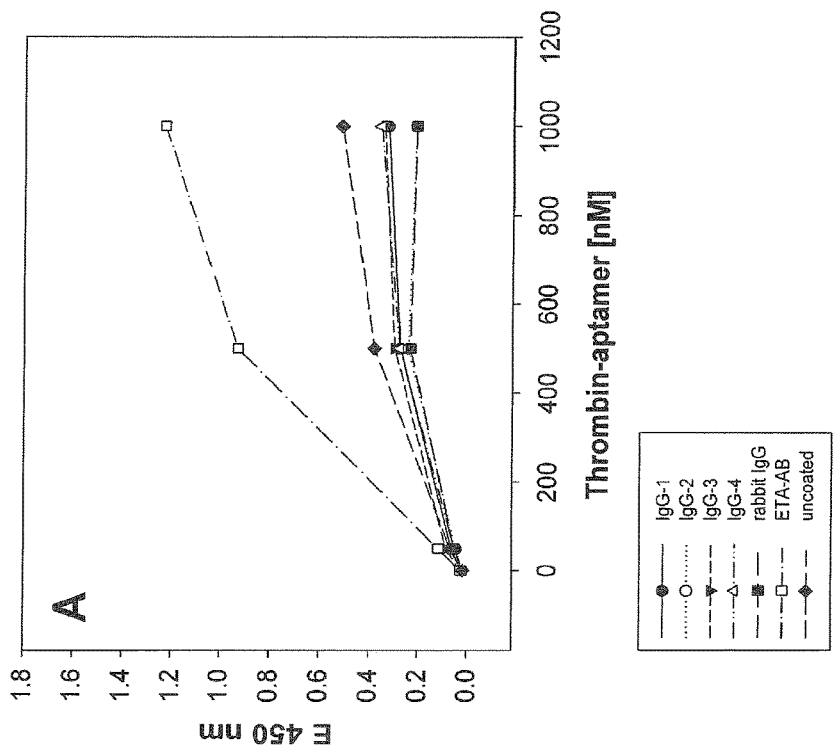
Figure 4:
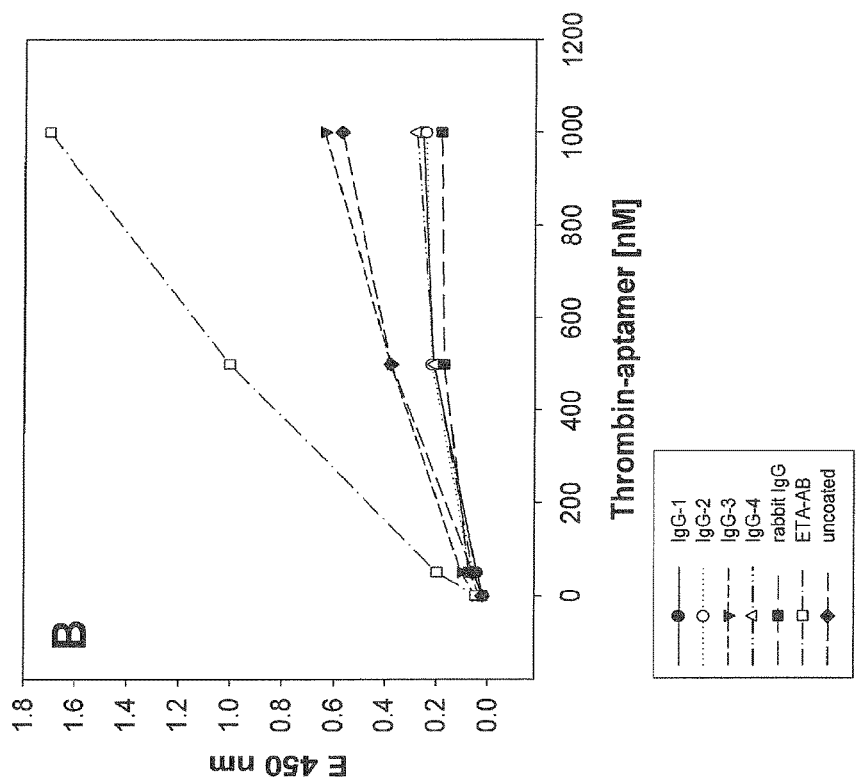
Figure 4:
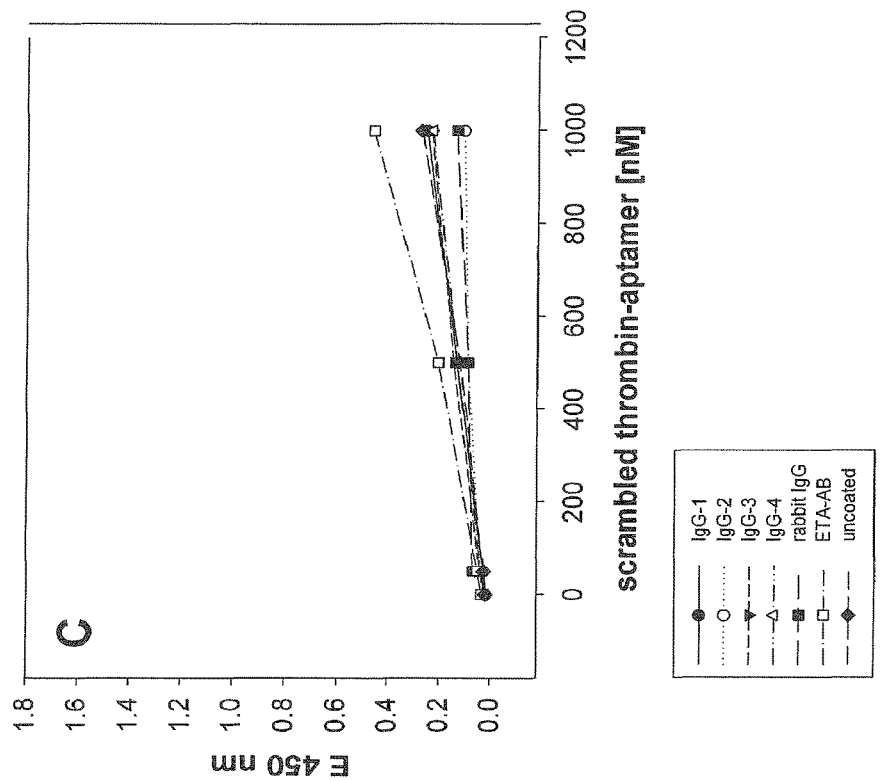
Figure 4:
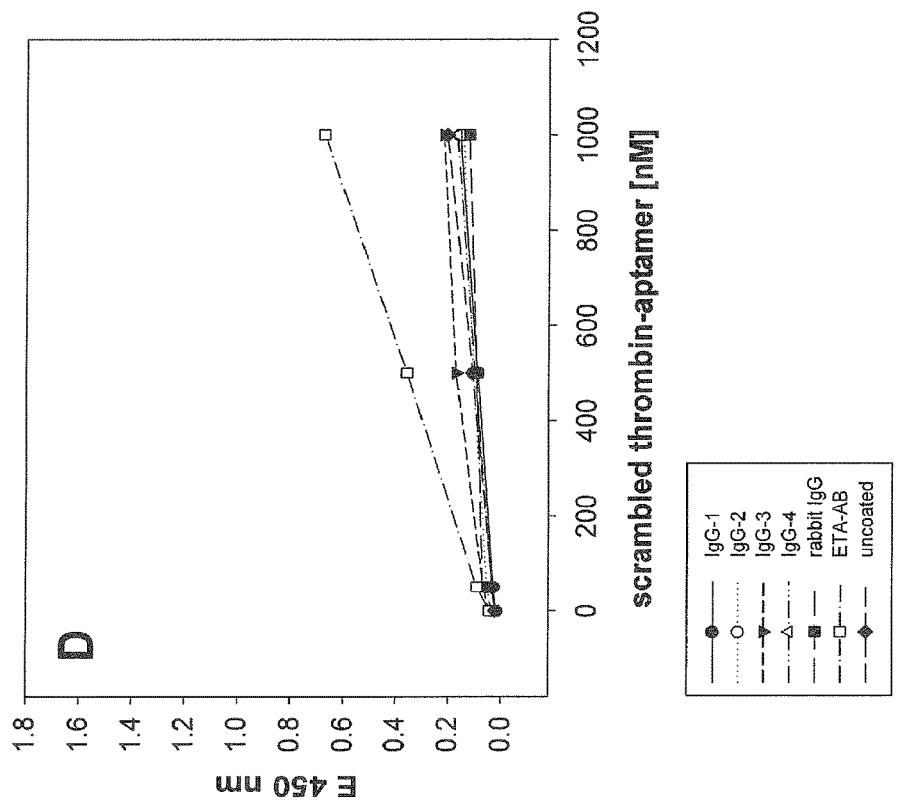

For the first set of experiments two different protein-concentrations for the immobilization onto the ELISA plate were chosen: 25 nM (FIG. 4A) and 250 nM (FIG. 4B). For control served rabbit IgG, human-IgG subclasses (IgG-1, 2, 3 and 4) at the same concentrations, and the uncoated plastic plate. A further control was the scrambled thrombin-aptamer sequence which was offered for binding (FIGS. 4C, 4D).

A second set of experiments tested the binding between the ETA-AB and the thrombin-aptamer SEQ. ID No. 1 in a vice versa experiment. Now the biotinylated thrombin-aptamer was immobilized onto the ELISA plates via preimmobilization of neutravidine. Afterwards the ETA-AB was offered for binding (FIGS. 5A, 5B).

Comparing the extinction between FIGS. 5B and 5A shows that a coating of 0.1 µM thrombin-aptamer (SEQ. ID No. 1) reached already the saturation in the given experiment.

A further control was the binding of the ETA-AB onto the immobilized scrambled thrombin-aptamer (FIG. 6).

The affinity of the ETA-AB towards the scrambled thrombin-aptamer was about 50% of the affinity reached if the thrombin-aptamer (SEQ. ID No. 1) was offered for binding.

Thombinaptamer-Column for the Removal of AAB from Serum Rabbit ETA-AB Spiked Human Serum In the following a thrombin-aptamer column was made which served for the removal of AAB from serum. For control served a column which carried the scrambled thrombin-aptamer.

The aptamers (thrombin-aptamer SEQ. ID No. 1) and scrambled control sequence were bound onto column material (NHS-activated Sepharose, GE healthcare) at a concentration of 0.1 µmol.

In a first set of experiments serum was spiked with the rabbit ETA-AB (50 nM) in order to obtain the chance to not only measure the ETA-AB activity via the bioassay (FIG. 7) but also via an ELISA (FIGS. 8A, 8B). The spiked sera were given over the column and the control column. The flow through was taken and stored. The bound ETA-ABs were eluted using a 3 M KSCN solution. Before measuring the AAB activity in the eluates, the samples were dialysed against physiologic buffer for 3 days at 4° C.

In the bioassay the eluates, which were taken in two fractions, were measured (FIG. 7). While the thrombin-aptamer column showed the ETA-AB activity after elution, the control column did not. The main ETA-AB fraction was in the second eluate fraction which was owed the used volumes. The volume of the column was 500 µl while for all handling steps 250 µl were chosen.

For the detection of the ETA-AB in the flow through or the eluate of the columns in the ELISA, the ETA-AB standard curve of the ELISA had also to undergo the dialyzation procedure, comparable to the eluate-sample material (FIG. 8A). Using this standard material, the samples were tested for the ETA-AB presence (FIG. 8B).

It is shown that only the specific thrombin-aptamer-column was able to bind the ETA-AB from the spiked control serum, while the scrambled control aptamer did not bind the ETA-AB. Here the ETA-AB was found in the flow through, while with the specific column the eluate fractions contained the ETA-AB.

Just to exclude that bound human IgG from the control serum might via cross reaction with the secondary antibody mimic ETA-AB presence, serum (40% and 100%) was also applied onto the ELISA plate. The maximal possible amount of cross reaction was measured, which was smaller than the specific anti-rabbit-AB detection. Moreover, it was shown in independent experiments that the eluates contained less than 1/10 human IgG compared to the flow through samples (data not shown), excluding an enormous influence of secondary antibody cross reactivity.

2. Human AAB Containing Serum

In a second series of experiments the thrombin-aptamer column was used for the removal of serum AAB. For control served the scrambled thrombin-aptamer column.

For this purpose 250 µl ETA-AAB and alpha1-receptor AAB containing serum was given over the columns. The flow throughs and the eluates were captured and estimated for AAB activity using the bioassay (Tab. 2). Elution was done with 3 M KSCN. The samples were dialyzed against a physiologic buffer for 3 days before the AAB-activity measurement was carried out.

TABLE 2

Measurement of the ETA-AAB and the alpha1-receptor AAB activity from human serum in the single fractions of the column experiment

| Decrease/increase in bead number [beads/15 sec] | | Thrombin-aptamer-column | Control column (scrambled tThrombin-aptamer) |
|---|---|---|---|
| Flow through | Alpha 1-receptor-AAB | −0.17 | 6.17 |
| | Endothelin-receptor-AAB | −0.17 | −4.17 |
| 1st eluate | Alpha 1-receptor-AAB | 2.0 | 0.17 |
| | Endothelin-receptor-AAB | −1.83 | 0.17 |
| 2nd eluate | Alpha 1-receptor-AAB | 4.67 | −0.17 |
| | Endothelin-receptor-AAB | −2.5 | −0.17 |
| 3rd eluate | Alpha 1-receptor-AAB | 1.0 | n.d. |
| | Endothelin-receptor-AAB | −0.5 | n.d. | n.d. = not determined

Possible Kit for Purification of Serum from AAB Via Aptamer-Magnetic Beads

A kit for either purification of serum from AAB or for the AAB-enrichment via thrombin-aptamer-magnetic beads.

TABLE 3

Binding of serum-AAB (human and rat) onto immobilized thrombin-aptamer (SEQ. ID No. 1; Streptavidin magnetic beads and biotinylated thrombin-aptamer)

| Delta Beads/ 15 sec | Thrombinapta (SEQ. ID No. 1) human β1-AAB | Scram-Thrombin Human β1-AAB | Thrombinapta (SEQ. ID No. 1) SHR-rat |
|---|---|---|---|
| Particle supernatant | 0 | 5.5 | 0 |
| 1. Washing solution | 0 | n.d. | 0 |
| 1st eluate | 5.67 (beta1receptor-AAB) | 1.0 (1st + 2nd eluate combined) | 4.67 (beta1-receptor-AAB) −1.83 (M2-receptor-AAB) |
| 2nd eluate | 2.5 (beta1-receptor-AAB) | | 2.5 (beta1-receptor-AAB) −2.83 (M2-receptor-AAB) |

Introduction of Exonuclease-Protection

In the following the influence of the introduction of a 3'-dT cap onto the functional activity of the aptamer SEQ. ID No. 1 was tested. A 3'-dT cap is thought to protect the nucleotide sequence from exonuclease activity and increases its stability in biological fluids. Testing the effect of the 3'-dT cap onto the aptamer functionality the beta1-receptor AAB (2. Loop) from a DCM patient and the beta2-receptor AAB from an Alzheimer patient were used (Tab 4). The functional activity of both AABs was neutralized when incubated with 100 nM of the 3'-dT cap modified aptamer. The 3'-cap-modification did not influence the functional activity of the aptamer SEQ. ID No. 1.

The CAP-protected aptamer alone did not influence the basal beating rate of the neonatale cardiomyocytes.

TABLE 4

Bioassay-measurement of the serum AAB chronotropic activity [delta beads/15 sec] of AABs treated with 3'-dT-cap modified thrombin-aptamer SEQ. ID No. 1 or not (without aptamer).

| disease | AAB-Typ | Without aptamer | +aptamer-3'-dT cap |
|---|---|---|---|
| DCM | Beta1-receptor-AAB | 6.0 | 0.0 |
| Alzheimer | Beta2-receptor-AAB | 5.17 | 0.0 |

FITC-Labelled Thrombin-Aptamer for the Detection of AABs

Use of Directly Fluorescence-Marker Labelled Thrombin-Aptamer for the Detection of Serum AABs The aim of these experiments is the generation of a directly labelled aptamer which targets autoantibodies against G-protein coupled receptors which will, at the end, be exploited for the detection of such AABs.

For this purpose the thrombin-aptamer was labeled at the 5'-end with FITC.

In first experiments it was tested, if the FITC-labelled thrombin-aptamer showed the full functionality/activity to neutralize autoantibodies compared to its unlabelled version. This was tested using the bioassay.

Figure 9:
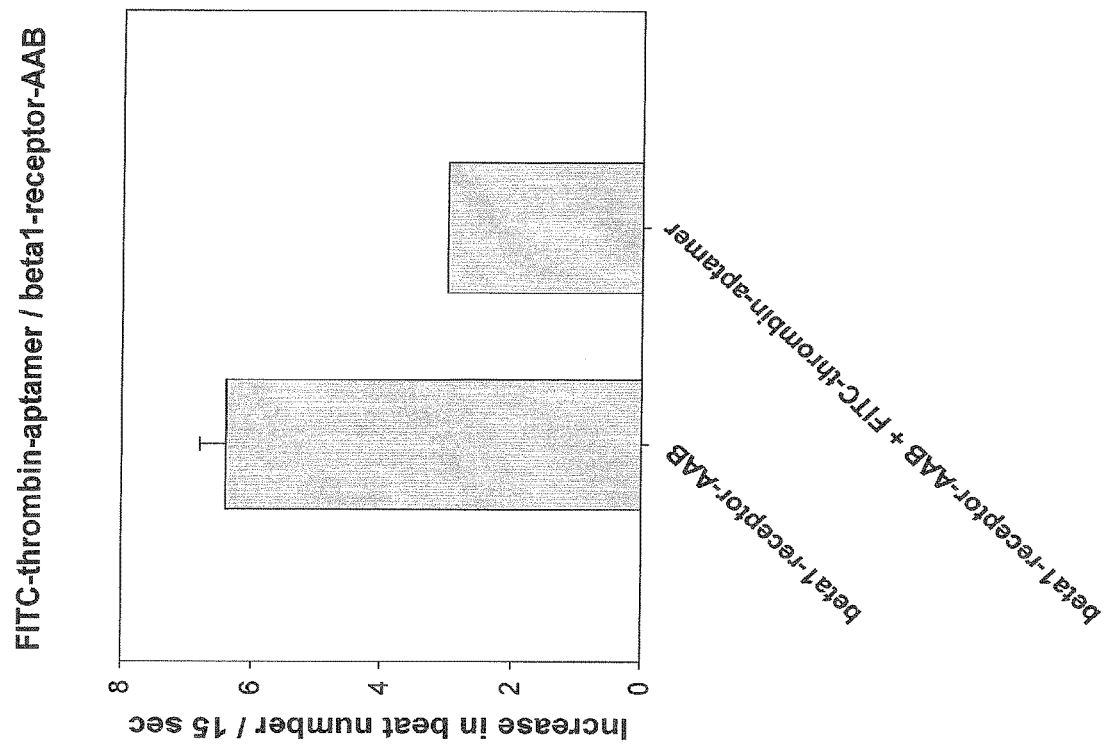

FIG. 9 shows the capacity of 100 nM of the 5'-FITC-thrombin-aptamer to neutralize beta1-receptor AABs. The FITC-label reduced the activity of the thrombin-aptamer, but 50% of the beta1-receptor AAB-activity was still neutralized at this chosen concentration of 100 nM. A partial inhibition of AAB activity was observed at this aptamer concentration.

Since the FITC-labelled thromnin-aptamer showed—if compared with the unlabeled aptamer at the same concentration—a partial inhibition of the AAB activity, the molecule was taken for testing, if it would be a possible strategy to use this labelled thrombin-aptamer for a sandwich assay. For this reason the unlabelled biotinylated thrombin-aptamer was immobilised on the ELISA-plate via Neutravidin and served for catching the AABs while the FITC-labelled anti.-thrombin-aptamer was supposed to serve at the end for the detection of the adsorbed AAB-material.

The samples were removed from the wells, the duplicates were unified (final volume 200 µl) and diluted with 300 µl PBS and the relative fluorescence was measured using the spectrofluorophotometer RF-5001PC (Shimadzu, Japan) using the excitation and emission wavelength of 494 nm and 519 nm, respectively.

Figure 10:
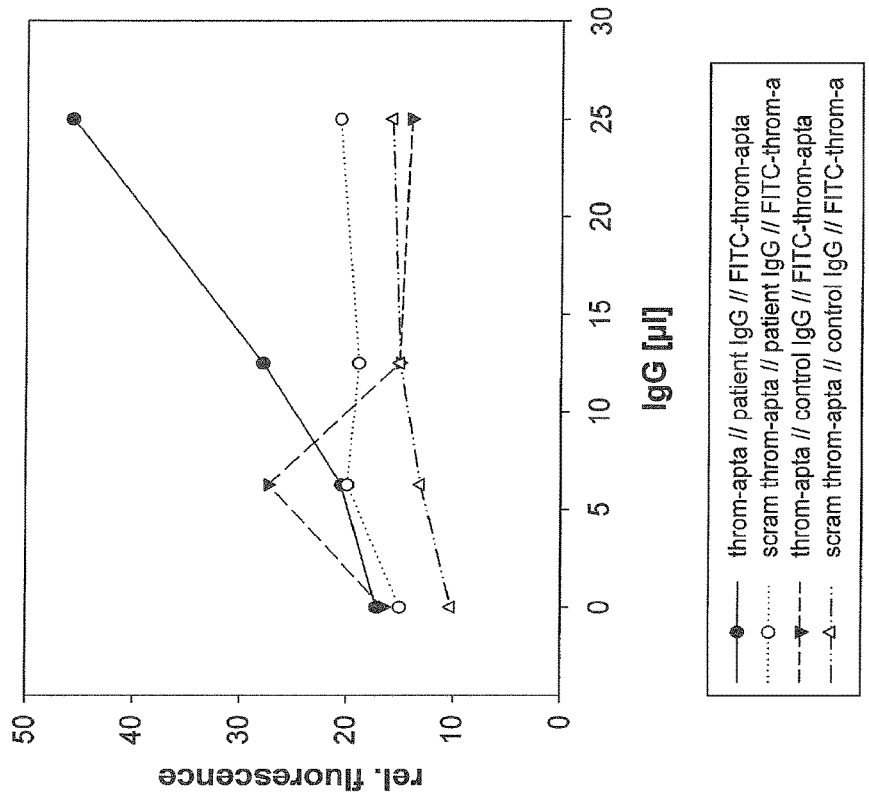

As to be seen from FIG. 10 it was possible to detect a patient sample (IgG-fraction containing ETA-AABs) compared to control IgG-sample. Using the scrambled thrombin-aptamer as a further control did also not show any fluorescence.

Influence of the dT-Cap on the Functionality of the Thrombin-Aptamer

Figure 11:
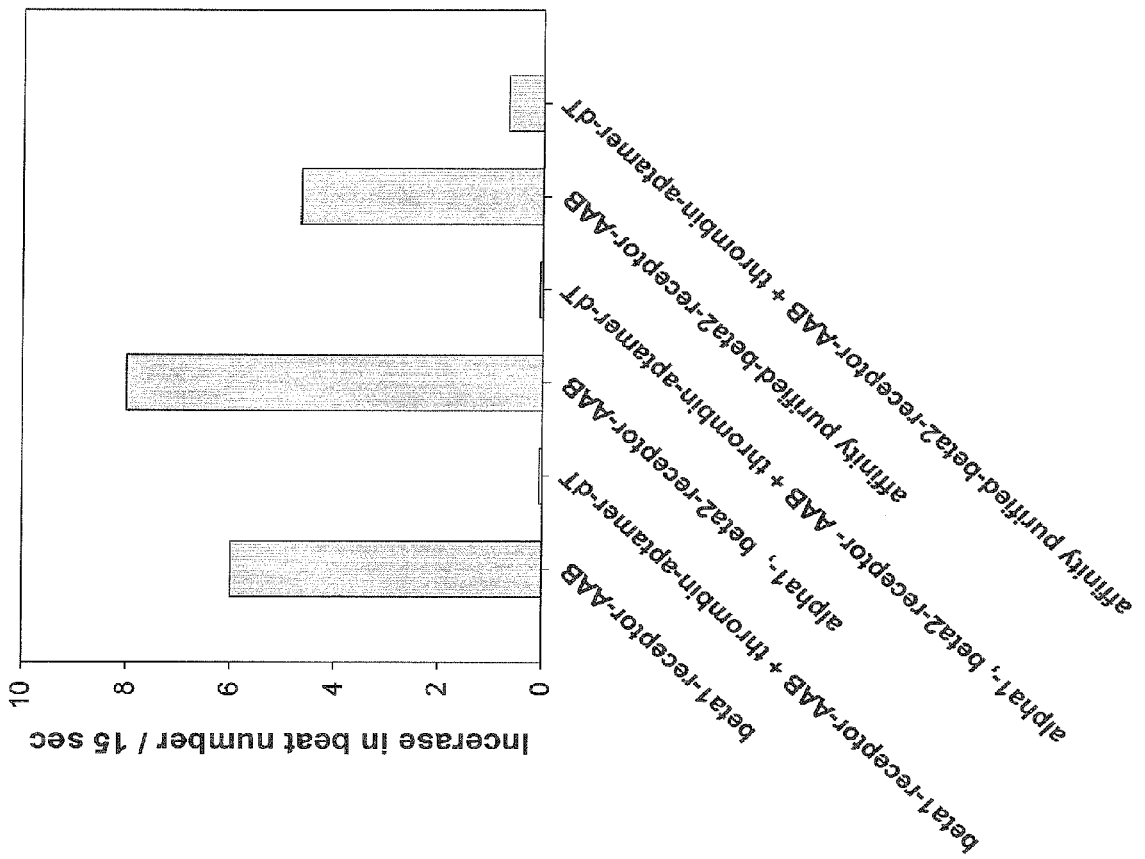

In next experiments it was tested, if the introduction of a protecting group such as the dT-cap for the protection from exonuclease activity would be possible, without influencing on the thrombin-aptamer activity neutralizing autoantibodies against G-protein coupled receptors. The introduction of a dT-cap was possible without influencing the thrombin-aptamer functionality to neutralize AABs against G-protein coupled receptors (FIG. 11).

Truncation of the Thrombin-Aptamer Resulting in 12mer Sequence

In a next set of experiments it was tested if a truncation of the thrombin-aptamer would result in products which are still able to neutralize autoantibodies against G-protein coupled receptors.

Figure 12:
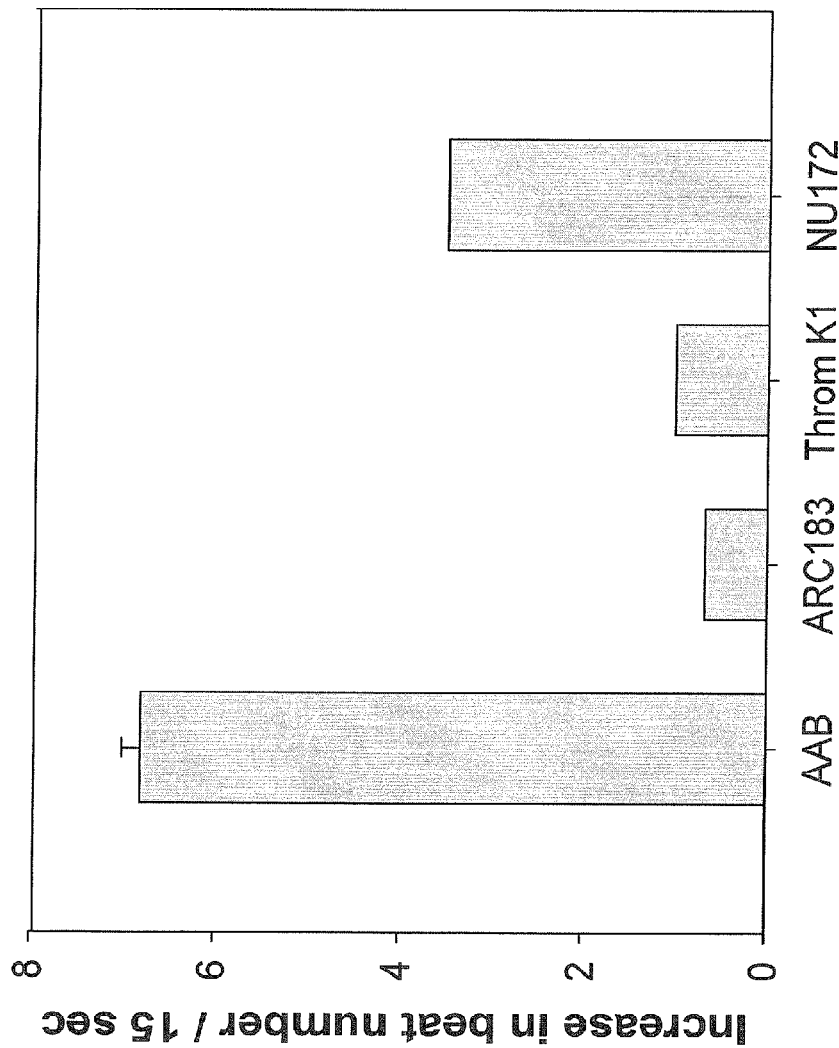

The original 15-mer sequence of the thrombin-aptamer (ARC183) was, therefore, truncated into a 12-mer sequence with SEQ ID No. 3, called Throm-K1. The truncated sequence was tested for its ability to neutralize AABs in the bioassay (demonstrated for beta1-receptor AABs, FIG. 12).

The 12-mer sequence showed full activity.

The invention claimed is:

1. A method of treatment or diagnosis of autoimmune diseases, wherein an individual suffering from an autoimmune disease is administered an effective amount of an aptamer comprising a nucleic acid sequence of SEQ ID No. 1, SEQ ID No. 2, SEQ ID No. 3 and/or a nucleic acid sequence being at least 80% identical to one of SEQ ID No. 1, 2 and 3 wherein autoantibodies specific for a G-protein coupled receptor are present in the serum of said individual suffering from said autoimmune disease, and wherein said aptamer binds specifically and with high affinity to said autoantibodies.

2. The method of claim 1, wherein the autoimmune disease is selected from the group consisting of: cardiomyopathy, dilated cardiomyopathy (DCM), peripartum cardiomyopathy (PPCM), idiopathic cardiomyopathy, Chagas' cardiomyopathy, Chagas' megacolon, Chagas' megaesophagus, Chagas' neuropathy, benign prostatic hyperplasia, scleroderma, psoriasis, Raynaud syndrome, pre-eclamsia, kidney allograft rejection, myocarditis, glaucoma, Diabetes mellitus, hypertension, pulmonary hypertension, malignant hypertension and Alzheimer's disease.

3. The method of claim 1, wherein the aptamer is used in treatment of a human.

4. The method of claim 1, wherein the aptamer is used in diagnosis of a human.

5. The method of claim 1, wherein the aptamer is used in treatment and diagnosis of a human.

6. The method of claim 1, wherein the aptamer is a DNA aptamer.

7. The method of claim 1, wherein the aptamer consists of the nucleic acid sequence of SEQ ID No. 1, SEQ ID No. 2, SEQ ID No. 3 or a nucleic acid sequence being at least 80% identical to one of SEQ ID No. 1, 2 and 3.

8. The method of claim 1, wherein the aptamer is administered as a pharmaceutical composition comprising the aptamer of claim 1 and at least one pharmaceutically acceptable excipient.

9. The method of claim 1, wherein the aptamer is provided as a kit comprising the aptamer of claim 1 and a container.

10. The method of claim 1, wherein the autoimmune disease is associated with the presence of autoantibodies specific for a G-protein coupled receptor.

* * * * *